United States Patent
Fan et al.

(10) Patent No.: US 10,174,023 B2
(45) Date of Patent: Jan. 8, 2019

(54) HETEROCYCLIC-IMIDAZOLE COMPOUNDS, PHARMACEUTICAL COMPOSITIONS THEREOF, PREPARATION METHOD THEREFOR AND USE THEREOF

(71) Applicant: SHANGHAI HUILUN LIFE SCIENCE & TECHNOLOGY CO., LTD, Shanghai (CN)

(72) Inventors: Xing Fan, Shanghai (CN); Jihong Qin, Shanghai (CN)

(73) Assignee: SHANGHAI HUILUN LIFE SCIENCE & TECHNOLOGY CO., LTD, Shanghai (CN)

( * ) Notice: Subject to any disclaimer, the term of this patent is extended or adjusted under 35 U.S.C. 154(b) by 0 days.

(21) Appl. No.: 15/567,359

(22) PCT Filed: Apr. 15, 2016

(86) PCT No.: PCT/CN2016/079489
§ 371 (c)(1),
(2) Date: Oct. 17, 2017

(87) PCT Pub. No.: WO2016/165655
PCT Pub. Date: Oct. 20, 2016

(65) Prior Publication Data
US 2018/0111927 A1    Apr. 26, 2018

(30) Foreign Application Priority Data
Apr. 17, 2015  (CN) .......................... 2015 1 0188965

(51) Int. Cl.
C07D 471/04    (2006.01)
A61K 31/52    (2006.01)
A61P 35/00    (2006.01)
C07D 487/04    (2006.01)

(52) U.S. Cl.
CPC ............ *C07D 471/04* (2013.01); *A61K 31/52* (2013.01); *A61P 35/00* (2018.01); *C07D 487/04* (2013.01)

(58) Field of Classification Search
CPC .................................................. C07D 471/04
See application file for complete search history.

(56) References Cited

FOREIGN PATENT DOCUMENTS

| CN | 1473154 A | 2/2004 |
|---|---|---|
| CN | 101048399 A | 10/2007 |
| CN | 102898378 A | 1/2013 |
| CN | 104003940 A | 8/2014 |

OTHER PUBLICATIONS

International Search Report and Written Opinion for PCT/CN2016/079489 dated Jul. 7, 2016.

*Primary Examiner* — Bruck Kifle
(74) *Attorney, Agent, or Firm* — Hunton Andrews Kurth LLP

(57) ABSTRACT

The present invention relates to heterocyclic-imidazole derivatives, a preparation method therefor, and a medical use thereof, and particularly to new heterocyclic-imidazole derivatives as represented by general formula (I), a preparation method therefor, pharmaceutical compositions comprising same, and a use thereof as a therapeutic agent, particularly as a poly(ADP-ribose)polymerase (PARP) inhibitor.

16 Claims, No Drawings

HETEROCYCLIC-IMIDAZOLE COMPOUNDS, PHARMACEUTICAL COMPOSITIONS THEREOF, PREPARATION METHOD THEREFOR AND USE THEREOF

CROSS-REFERENCE TO RELATED APPLICATIONS

The present application is a National Stage Application under 35 U.S.C. 371 of PCT/CN2016/079489, filed Apr. 15, 2016, which claims priority to Chinese Application Number 2015101889652, filed on Apr. 17, 2015. The contents of each of these applications is incorporated herein by reference for all purposes.

BACKGROUND

Technical Field

The present invention relates to a heterocyclic-imidazole derivative, a preparation method, a pharmaceutical composition containing the same, and use thereof as a therapeutic agent and a poly(ADP-ribose) polymerase (PARP) inhibitor.

Related Art

Chemotherapeutics and ionizing radiation are two ways commonly used in the treatment of cancers. The two therapies both cause DNA single strand and/or double strand break, and thus exert a cytotoxic effect, resulting in the death of target tumor cells due to chromosome damage. In response to DNA damage, an important consequence is the activation of cell cycle checkpoint signaling for the purpose of protecting the cells against mitosis in case of DNA damage, thereby avoiding cell damage. In most cases, the tumor cells have a high proliferation rate while exhibiting deficiency in cell cycle checkpoint signaling. Therefore, it can be inferred that a specific mechanism of DNA repair exists in the tumor cells, which may rapidly respond to and repair the chromosome damage associated with proliferation regulation, such that the tumor cells survive the cytotoxic effect of some therapeutic agent.

In clinical use, the concentration of the chemotherapeutic agent or the intensity of the radiation is effective for counteracting the mechanism of DNA repair, to ensure the killing effect on target tumor cells. However, resistance to treatment may be developed in the tumor cells through a strengthened mechanism of DNA damage repair, such that the tumor cells survive the fatal DNA damage. To overcome the resistance development, the dose of the therapeutic agent or the intensity of the radiation is generally required to be enhanced. This has a detrimental effect on normal tissues around the lesion, whereby serious adverse effects are implicated during treatment, and the treatment risk is increased. Meanwhile, the therapeutic effect is decreased with increasing resistance. Therefore, it can be inferred that the cytotoxic effect of a DNA damaging agent may be improved in a tumor cell-specific manner by regulating the DNA damage signaling and repair mechanism.

Poly(ADP-ribose)polymerases (PARPs) characterized by poly(ADP-ribosyl)ation activity constitute a super family of 18 intranuclear and cytoplasmic enzymes. Through this poly(ADP-ribosyl)ation, the catalytic activity of target proteins and the protein-protein interactions may be modulated, and some fundamental biological processes are regulated, including DNA repair, and cell death. Moreover, the genomic stability also correlates with the poly(ADP-ribosyl)ation.

PARP-1 activity accounts for about 80% of the total PARP activity in the cells. PARP-1 and PARP-2 closest thereto are members in the PARP family that have an ability to repair the DNA damage. As a sensor and signaling protein of DNA damage, PARP-1 can quickly detect and directly bind to the site of DNA damage, followed by inducing the aggregation of numerous proteins required for DNA repair, such that the DNA damage is repaired. When PARP-1 is deficient in the cells, PARP-2 is able to repair the DNA damage in place of PARP-1. Studies show that compared with normal cells, PARPs are expressed at a generally increased level in solid tumors. Furthermore, cancers (e.g. breast and ovary cancer) which are deficient in DNA repair-related genes (e.g. BRCA-1 or BRCA-2) are extremely sensitive to the PARP-1 inhibitor, indicating that the PARP inhibitor, as a single therapeutic agent, is potentially useful in the treatment of triple negative breast cancer. Moreover, since the mechanism of DNA damage repair is a principal mechanism through which resistance is developed in the tumor cells counteracting the chemotherapeutic agent and ionizing radiation. Accordingly, PARP-1 is considered to be a target of interest in seeking a new method for treating cancers.

The PARP inhibitors that are developed and designed previously are analogues developed with nicotinamide of NAD that is a substrate for PARP as a template. These inhibitors are competitive inhibitors of NAD, which compete with NAD for the catalytic sites of PARP, thereby hindering the synthesis of poly(ADP-ribose) chain. Without the modification with poly(ADP-ribosyl)ation, PARP cannot be cleaved from the site of DNA damage, such that other proteins involved in repair cannot access the site of damage and thus the repair process cannot be performed. Therefore, under attack of cytotoxic agents or radiation, the presence of the PARP inhibitor ultimately leads to the death of tumor cells with impaired DNA.

In addition, NAD, consumed as a substrate for PARP, is essential to the synthesis of ATP in cells. At a high level of PARP activity, the intracellular NAD level decreases dramatically, thus affecting the ATP level in cells. Due to the inadequate content of ATP in the cells, the cells are failed in ATP-dependent programmed cell death, and have to turn to necrosis, a special apoptosis process. During necrosis, a large amount of inflammatory factors are released, causing a toxic effect to other organs and tissues. Therefore, the PARP inhibitor may find use in the treatment of many diseases associated with such a mechanism, including neurodegenerative diseases (for example, senile dementia, Huntington's disease, and Parkinson's disease), diabetes, ischemia or complications during ischemic reperfusion, for example, myocardial infarction and acute renal failure, diseases of circulatory system, for example, septic shock, and inflammatory diseases such as chronic rheumatism.

Among a total of 14 PARP inhibitors in clinical research, AZD2281 (with a structural formula below) developed by AstraZeneca was approved by FDA in December 2014 for treating end-stage ovarian cancer patients with indications sensitive to platinum-based chemotherapy. Relevant patent applications include WO2002036576 and WO2006021801.

AZD2281

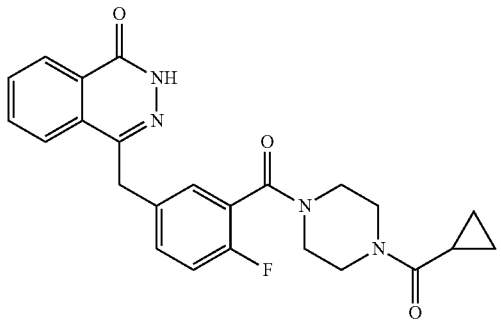

(I)

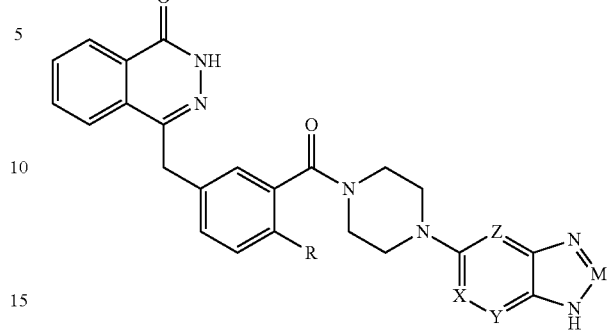

Although a series of PARP inhibitors have been disclosed at present, there is still a need to develop a new compound with better efficacy, better pharmacokinetic properties, and lower toxicity. After unremitting efforts, the present invention relates to a compound of general Formula (I) and the compound having such a structure is found to exhibit excellent effects and actions.

SUMMARY

A first objective of the present invention is to provide a new heterocyclic-imidazole compound of general Formula (I), or a pharmaceutically acceptable salt thereof.

A second objective of the present invention is to provide a method for preparing the heterocyclic-imidazole compound, or a pharmaceutically acceptable salt thereof.

A third objective of the present invention is to provide an intermediate useful in the preparation of the heterocyclic-imidazole compound, or a pharmaceutically acceptable salt thereof.

A fourth objective of the present invention is to provide a method for preparing the intermediate useful in the preparation of the heterocyclic-imidazole compound, or a pharmaceutically acceptable salt thereof.

A fifth objective of the present invention is to provide use of the intermediate in the preparation of the compound of general Formula (I) and a derivative thereof.

A sixth objective of the present invention is to provide a pharmaceutical composition comprising the heterocyclic-imidazole compound, or a pharmaceutically acceptable salt thereof as an active ingredient.

A seventh objective of the present invention is to provide use of the heterocyclic-imidazole compound, or a pharmaceutically acceptable salt thereof in the preparation of drugs.

In a first aspect of the present invention, a heterocyclic-imidazole compound of general Formula (I) or a pharmaceutically acceptable salt thereof is provided:

where in general Formula (I)

R is hydrogen, halo, $C_1$-$C_6$ alkoxy or $C_1$-$C_6$ haloalkyl;

one of X, Y, and Z is nitrogen, and the others are CH; or one of X, Y, and Z is CH, and the others are nitrogen; and M is nitrogen or $CR_1$, in which $R_1$ is hydrogen, oxygen, $C_1$-$C_6$ alkyl or $C_1$-$C_6$ haloalkyl.

Further preferably, in the compound of general Formula (I) provided in the present invention R is hydrogen, fluoro, methoxy or trifluoromethyl;

one of X, Y, and Z is nitrogen, and the others are CH; or one of X, Y, and Z is CH, and the others are nitrogen; and M is nitrogen or $CR_1$, in which $R_1$ is hydrogen, oxygen, methyl or trifluoromethyl.

In a specific embodiment of the present invention, a compound of general Formula (I) is provided, in which R is hydrogen, halo, $C_1$-$C_3$ alkoxy or $C_1$-$C_3$ haloalkyl.

In a specific embodiment of the present invention, a compound of general Formula (I) is provided, in which R is hydrogen, fluoro, methoxy or trifluoromethyl.

In a specific embodiment of the present invention, a compound of general Formula (I) is provided, in which X and Z are nitrogen, and Y is CH; or X is nitrogen, and Y and Z are CH; or Z is nitrogen, and X and Y are CH; or Y is nitrogen, and X and Z are CH.

In a specific embodiment of the present invention, a compound of general Formula (I) is provided, in which $R_1$ is hydrogen, oxygen or $C_1$-$C_6$ alkyl or $C_1$-$C_6$ haloalkyl.

In a specific embodiment of the present invention, a compound of general Formula (I) is provided, in which $R_1$ is hydrogen, oxygen or $C_1$-$C_3$ alkyl or $C_1$-$C_3$ haloalkyl.

In a specific embodiment of the present invention, a compound of general Formula (I) is provided, in which $R_1$ is hydrogen, oxygen or methyl or trifluoromethyl.

In a preferred embodiment of the present invention, the heterocyclic-imidazole compound of general Formula (I) is a 4-(3-(piperazine-1-carbonyl)benzyl)phthalazin-1(2H)-one compound and a pharmaceutically acceptable salt thereof.

Most preferably, the compound of general Formula (I) according to the present invention is selected from the group consisting of Compounds (1) to (21) below:

(1)
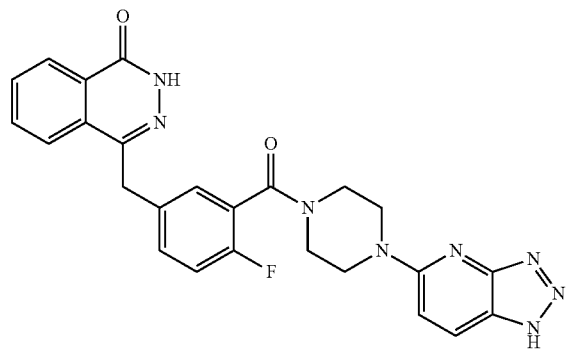
(2)
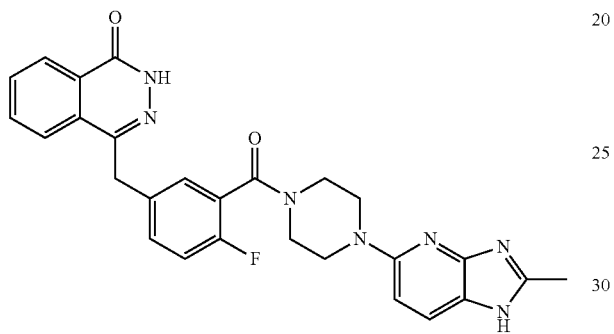
(3)
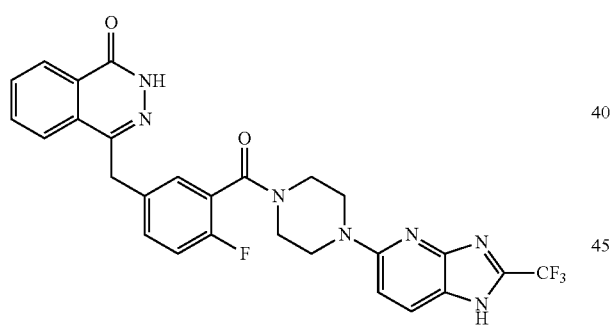
(4)
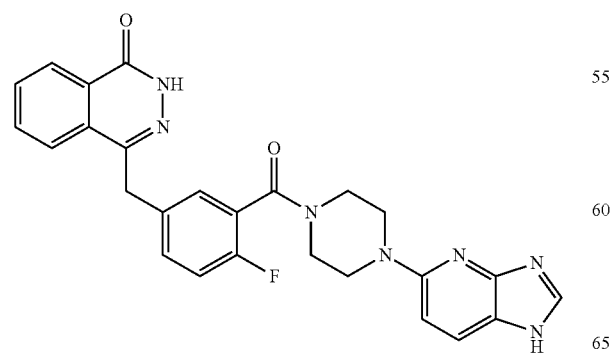
(5)
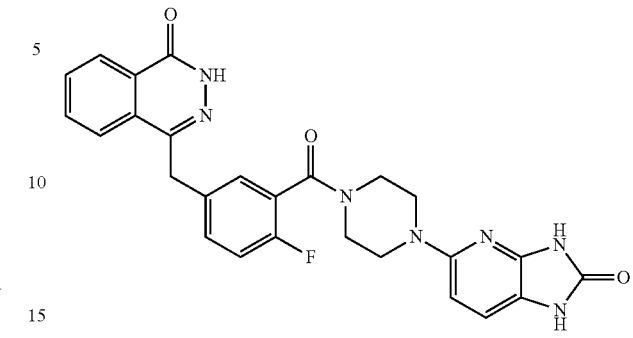
(6)
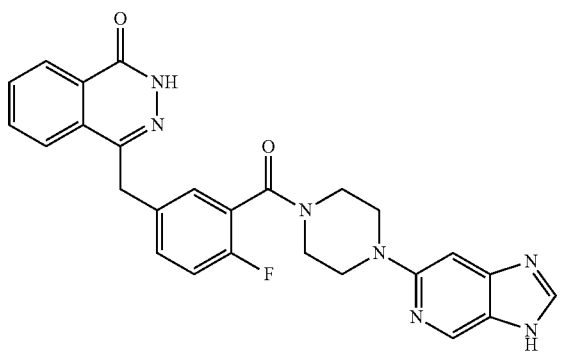
(7)
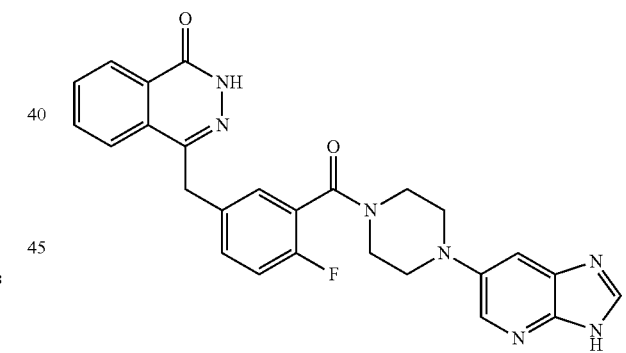
(8)
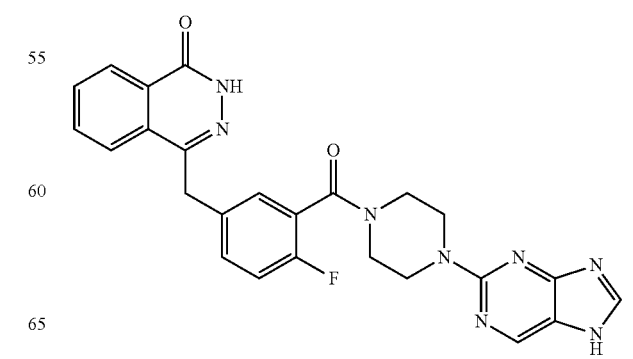

(9)
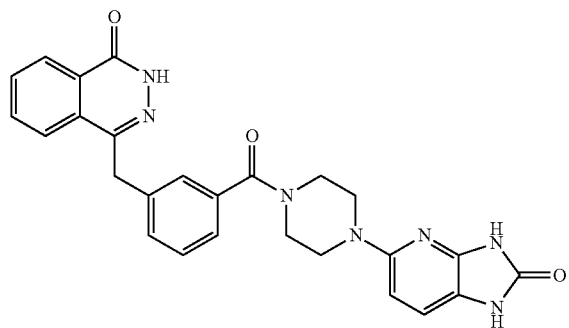
(10)
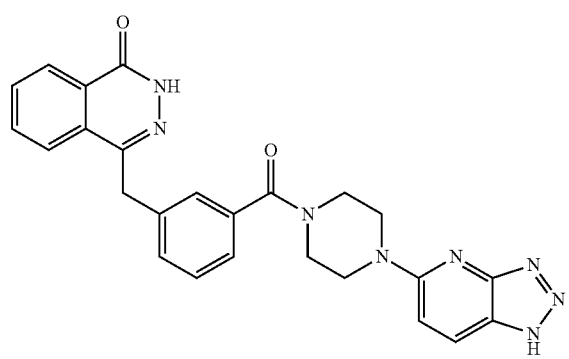
(11)
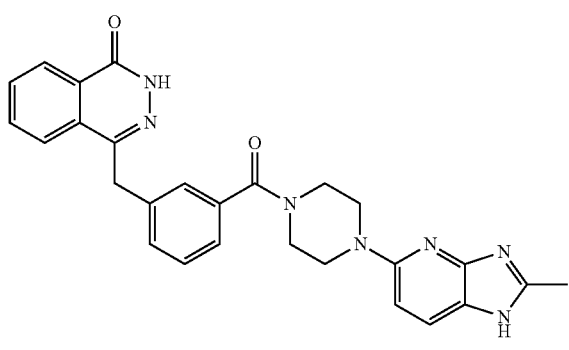
(12)
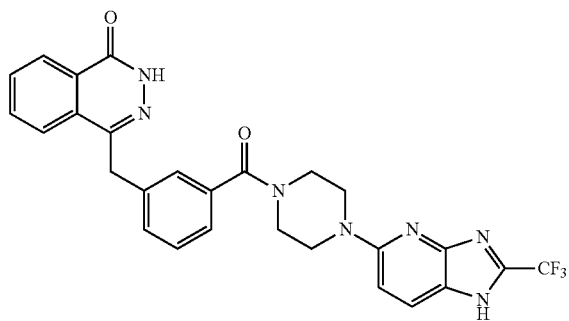
(13)
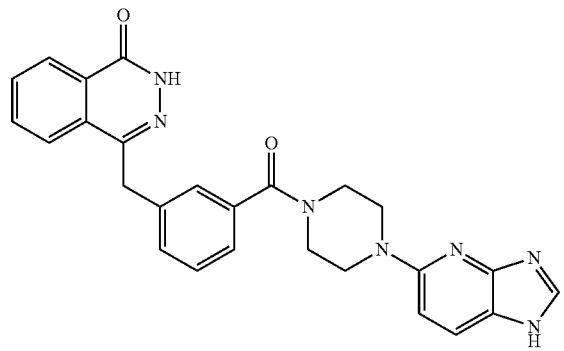
(14)
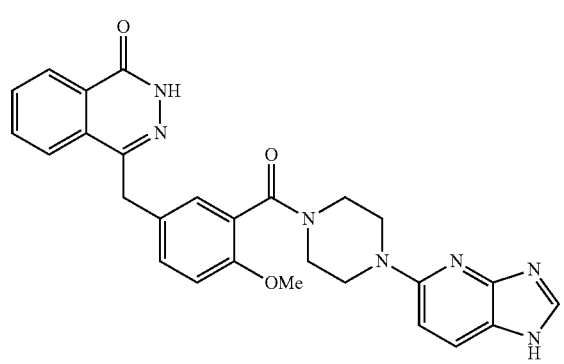
(15)
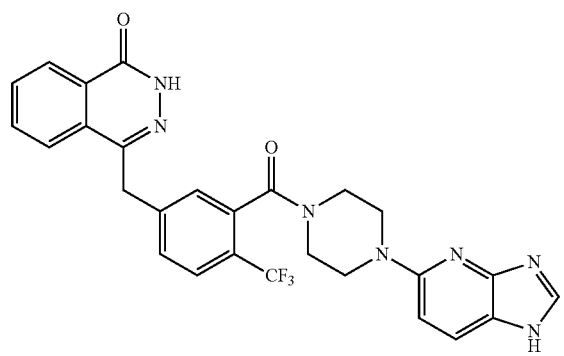
(16)
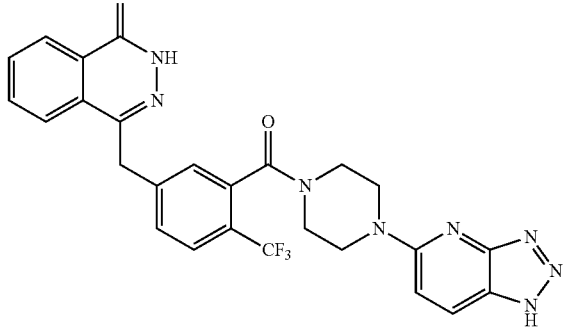

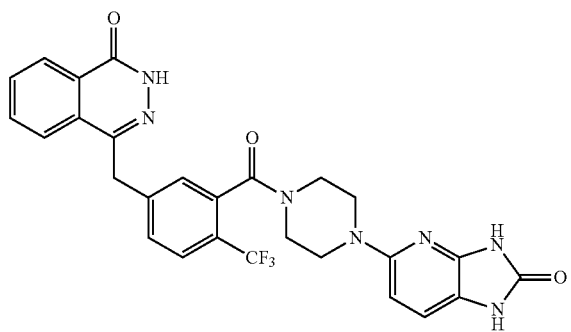

(17)

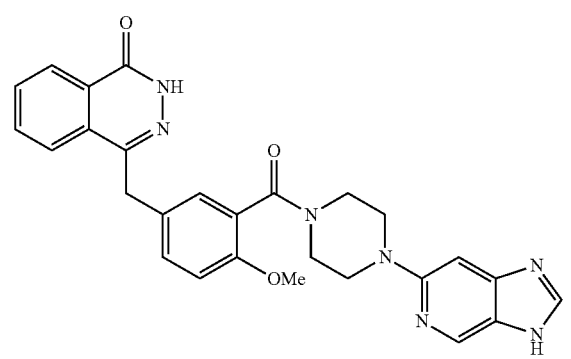

(18)

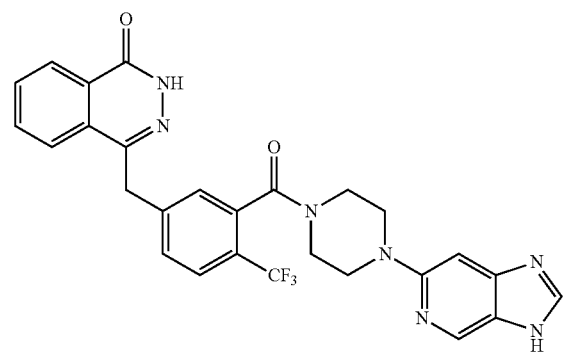

(19)

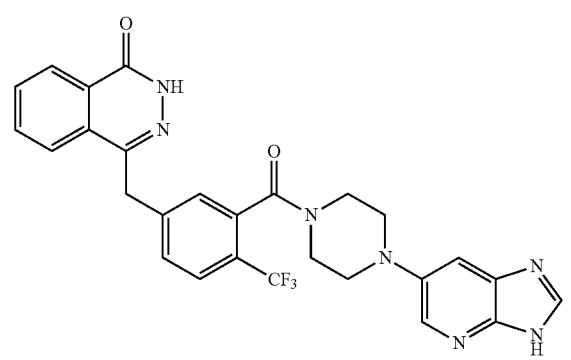

(20)

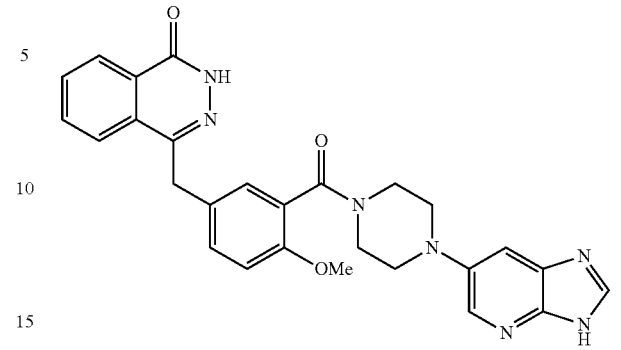

(21)

The compound of general Formula (I) is in the form of a tautomer, an enantiomer, a diastereomer, a mesomer, a racemate, and a mixture thereof.

The compound of general Formula (I) is a pharmaceutically acceptable derivative.

The compound of general Formula (I) according to the present invention may exist as a pharmaceutically acceptable salt. In a second aspect of the present invention, a method for preparing the compound of general Formula (I) is provided. The reaction scheme is as follows:

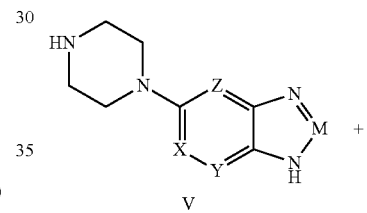

V

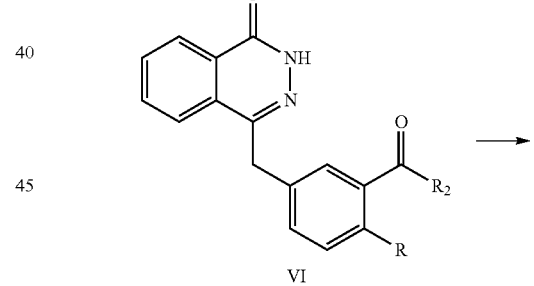

VI

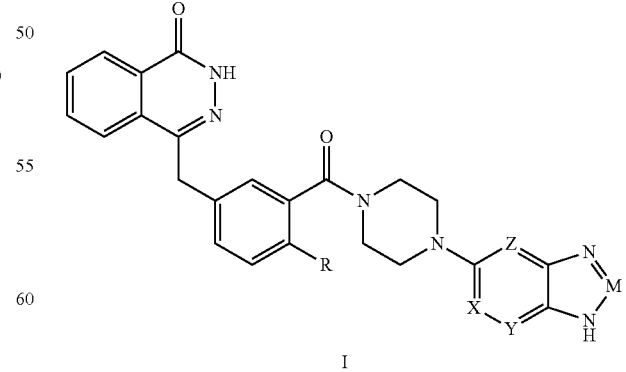

I where R, X, Y, Z and M are as defined above; and $R_2$ is hydroxyl, halo, or biimidazol-1-yl. The method comprises specifically:

condensing an Intermediate (V) with a phthalazinecarboxylic acid derivative (VI), to produce a compound of general Formula (I).

In a specific embodiment of the present invention, the Intermediate (V) is prepared through a process comprising:

Step 1): subjecting a mono-protected piperazine to nucleophilic substitution with a heterocyclic halide substituted with an amino or nitro group, to obtain an Intermediate (II);

Step 2): catalytically hydrogenating the Intermediate (II) to reduce the nitro group, so as to obtain an Intermediate (III);

Step 3): cyclizing the Intermediate (III) with acetic anhydride, trifluoroacetic anhydride, trimethyl orthoformate, carbonyl diimidazole or an azide compound, to obtain an Intermediate (IV); and Step 4): deprotecting the amino group in the Intermediate (IV), to obtain an Intermediate (V).

The reaction scheme is shown below:

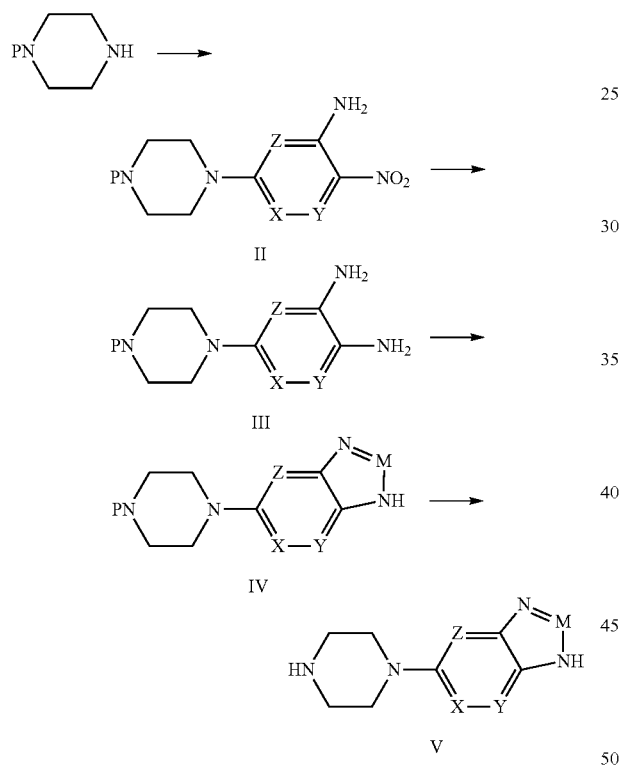

where P is an amino-protecting group, and one of X, Y, and Z is nitrogen, and the others are CH; or one of X, Y, and Z is CH, and the others are nitrogen;

M is nitrogen or $CR_1$;

$R_1$ is hydrogen, oxygen, methyl or trifluoromethyl.

In a specific embodiment of the present invention, a compound of general Formula (I) is provided, in which X and Z are nitrogen, Y is CH; or X is nitrogen, and Y and Z are CH; or Z is nitrogen, and X and Y are CH; or Y is nitrogen, and X and Z are CH.

In a specific embodiment of the present invention, a compound of general Formula (I) is provided, in which $R_1$ is hydrogen, oxygen, $C_1$-$C_6$ alkyl or $C_1$-$C_6$ haloalkyl.

In a specific embodiment of the present invention, a compound of general Formula (I) is provided, in which $R_1$ is hydrogen, oxygen, $C_1$-$C_3$ alkyl or $C_1$-$C_3$ haloalkyl.

In a specific embodiment of the present invention, a compound of general Formula (I) is provided, in which $R_1$ is hydrogen, oxygen, methyl or trifluoromethyl.

Preferably, the phthalazinecarboxylic acid derivative (VI) is a compound shown below:

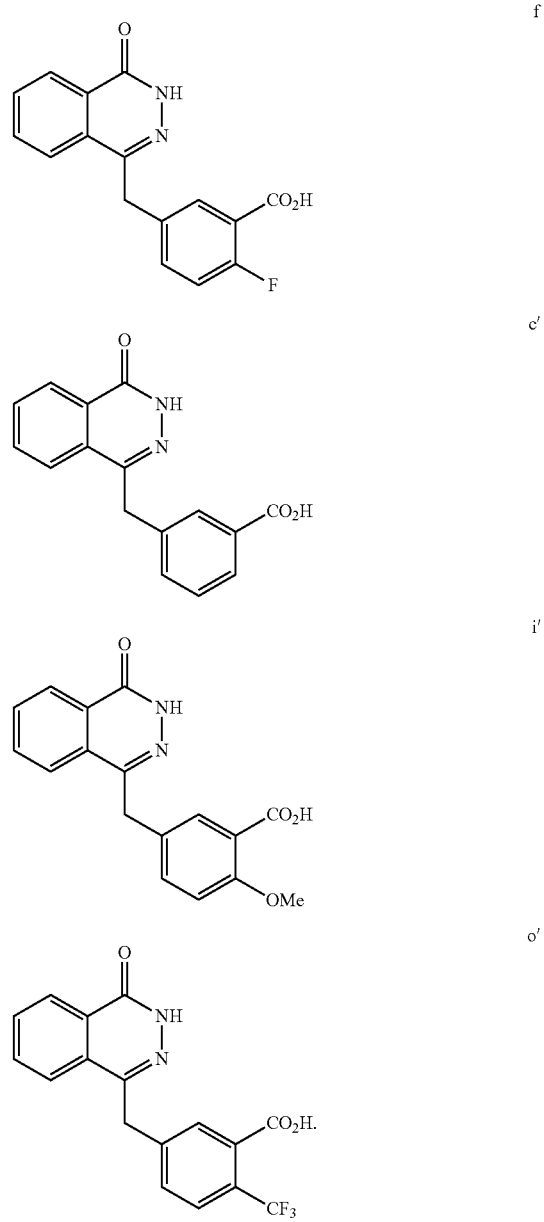 [SMILES: O=C(O)c1cc(Cc2n[nH]c(=O)c3ccccc23)ccc1F ; O=C(O)c1cccc(Cc2n[nH]c(=O)c3ccccc23)c1 ; COc1ccc(Cc2n[nH]c(=O)c3ccccc23)cc1C(=O)O ; O=C(O)C1=CC(Cc2n[nH]c(=O)c3ccccc23)CC=C1C(F)(F)F]

Preferably, the Intermediate V is a compound shown below:

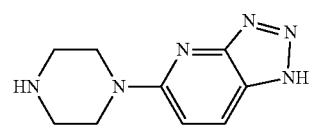

-continued

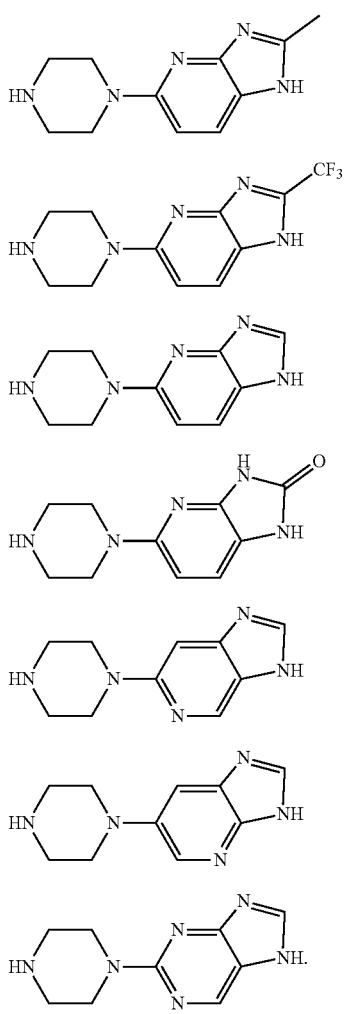

In a specific embodiment of the present invention, the condensing agent used in the condensation reaction is selected from the group consisting of 1,1'-carbonyl diimidazole, 1-ethyl-(3-dimethylaminopropyl) carbodiimide hydrochloride, 2-(7-azabenzotriazolyl)-N,N,N',N'-tetramethyluronium hexafluorophosphate, and benzotriazole-N,N,N',N'-tetramethyluronium hexafluorophosphate.

In a specific embodiment of the present invention, the solvent used in the condensation reaction is selected from the group consisting of dichloromethane, ethyl acetate, dimethyl sulfoxide, tetrahydrofuran, dimethyl formamide, dimethyl acetamide, N-methylpyrrolidone, and acetone.

In a specific embodiment of the present invention, an inorganic or organic base is added to the condensation reaction reaction.

In a specific embodiment of the present invention, the organic base is selected from the group consisting of triethylamine, diethylamine, diisopropylethylamine, and piperidine.

In a specific embodiment of the present invention, the Intermediate (III) is cyclized with sodium nitrite, acetic anhydride, trifluoroacetic anhydride, trimethyl orthoformate or an azide compound, to obtain the Intermediate (IV).

In a specific embodiment of the present invention, the Intermediate (III) is cyclized with acetic anhydride, trifluoroacetic anhydride, trimethyl orthoformate or sodium azide, to obtain the Intermediate (IV).

In a third aspect of the present invention, an intermediate for preparing a heterocyclic-imidazole compound of general Formula (I) is provided, which is a compound of structural Formula (V):

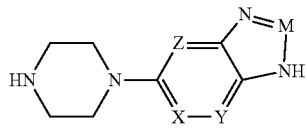

where in Intermediate (V):
one of X, Y, and Z is nitrogen, and the others are CH; or one of X, Y, and Z is CH, and the others are nitrogen; and
M is nitrogen or $CR_1$, in which
$R_1$ is hydrogen, oxygen, alkyl, alkoxy or haloalkyl.

In a specific embodiment of the present invention, X and Z are nitrogen, and Y is CH; or X is nitrogen, and Y and Z are CH; or Z is nitrogen, and X and Y are CH; or Y is nitrogen, and X and Z are CH.

In a specific embodiment of the present invention, $R_1$ is hydrogen, oxygen, $C_1$-$C_6$ alkyl or $C_1$-$C_6$ haloalkyl.

In a specific embodiment of the present invention, $R_1$ is hydrogen, oxygen, $C_1$-$C_3$ alkyl or $C_1$-$C_3$ haloalkyl.

In a specific embodiment of the present invention, $R_1$ is hydrogen, oxygen, methyl or trifluoromethyl.

Particularly preferably, the Intermediate (V) is a compound shown below:

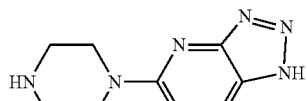

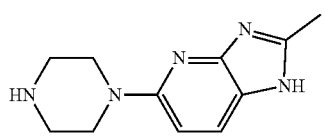

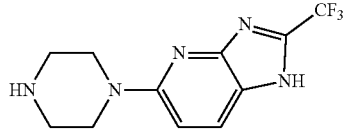

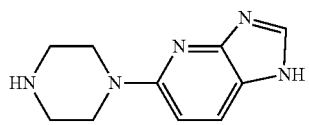

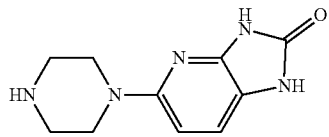

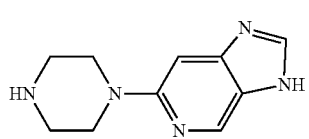

-continued

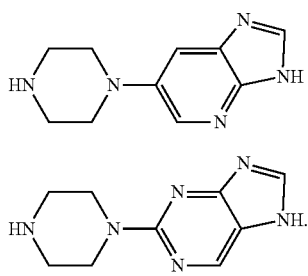

In a fourth aspect of the present invention, a method for preparing the Intermediate (V) is provided, which comprises:

Step 1): subjecting a mono-protected piperazine to nucleophilic substitution with a heterocyclic halide substituted with an amino or nitro group, to obtain an Intermediate (II);

Step 2): catalytically hydrogenating the Intermediate (II) to reduce the nitro group, so as to obtain an Intermediate (III);

Step 3): cyclizing the Intermediate (III) with sodium nitrite, acetic anhydride, trifluoroacetic anhydride, trimethyl orthoformate, or an azide compound, to obtain an Intermediate (IV); and Step 4): deprotecting the amino group in the Intermediate (IV), to obtain an Intermediate (V).

The reaction scheme is shown below:

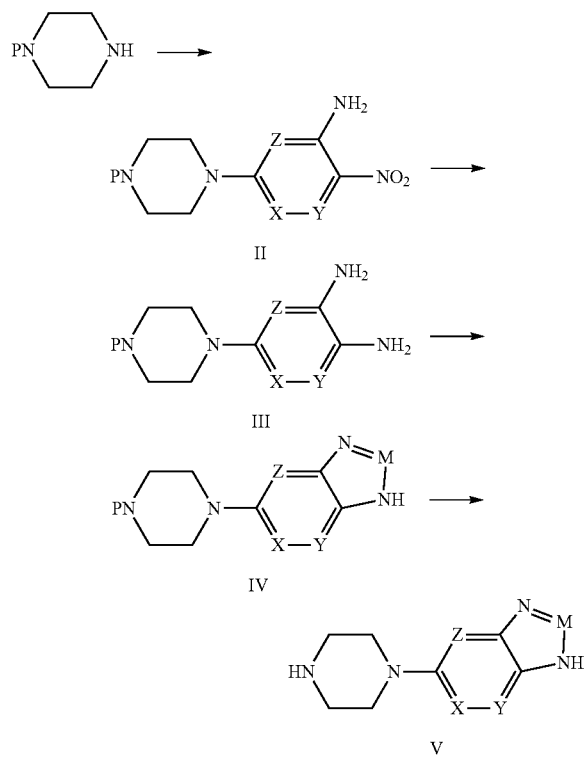

where P is an amino-protecting group; one of X, Y, and Z is nitrogen, and the others are CH; or one of X, Y, and Z is CH, and the others are nitrogen; and M is nitrogen or $CR_1$, in which $R_1$ is hydrogen, oxygen, methyl or trifluoromethyl.

In a specific embodiment of the present invention, the Intermediate (III) is cyclized with acetic anhydride, trifluoroacetic anhydride, trimethyl orthoformate or sodium azide, to obtain the Intermediate (IV).

In a fifth aspect of the present invention, use of the Intermediate (V) in the preparation of a compound of general Formula (I) or a pharmaceutically acceptable salt thereof is provided.

In a sixth aspect of the present invention, a pharmaceutical composition is provided, which comprises a therapeutically effective amount of a compound of general Formula I or a pharmaceutically acceptable salt thereof as an active ingredient, and one or more pharmaceutically acceptable carriers, excipients and/or diluents The pharmaceutical composition is formulated into tablets, capsules, an aqueous suspension, an oily suspension, a dispersible powder, granules, lozenges, an emulsion, a syrup, a cream, suppositories or injections.

In the pharmaceutical composition, the compound of general Formula (I) exists in a free form.

In a seventh aspect of the present invention, use of the compound of general Formula (I) or a pharmaceutically acceptable salt thereof in the preparation of drugs for treating diseases that are ameliorated through inhibition of the PARP activity is provided.

In the seventh aspect of the present invention, used of the pharmaceutical composition in the preparation of drugs for treating diseases that are ameliorated through inhibition of the PARP activity is provided.

The diseases that are ameliorated through inhibition of the PARP activity include vascular diseases, septic shock, ischemic damage, neurotoxic symptoms, hemorrhagic shock, inflammatory disease, multiple sclerosis, neurodegenerative diseases, or diabetes. Studies on the relation between the diseases and the PARP activity are carried out by Cantoni et al. (Biochim. Biophys. Acta, 1989, 1014: 1-7) and Liaudet et al (Proc. Natl. Acad. Sci. U.S.A., 97 (3), 2000, 97 (3): 10203-10208).

In the seventh aspect of the present invention, use of the compound of general Formula (I) in the preparation of adjuvant drugs for treating tumors is provided.

In the seventh aspect of the present invention, use of the compound of general Formula (I) or a pharmaceutically acceptable salt thereof in the preparation of adjuvant drugs for treating tumors is provided.

In the seventh aspect of the present invention, use of the pharmaceutical composition in the preparation of adjuvant drugs for treating cancers is provided.

In the seventh aspect of the present invention, use of the compound of general Formula (I) in the preparation of chemotherapeutics for treating cancers or drugs for boosting the cancer radiotherapy is provided.

In the seventh aspect of the present invention, use of the compound of general Formula (I) or a pharmaceutically acceptable salt thereof in the preparation of chemotherapeutics for treating cancers or drugs for boosting the cancer radiotherapy is provided.

In the seventh aspect of the present invention, use of the pharmaceutical composition in the preparation of chemotherapeutics for treating cancers or drugs for boosting the cancer radiotherapy is provided.

In the seventh aspect of the present invention, use of the compound of general Formula (I) in the preparation of drugs for treating a subject with a cancer that is deficient in Homologous Recombination (HR) dependent DNA double strand break (DSB) repair is provided.

In the seventh aspect of the present invention, use of the compound of general Formula (I) or a pharmaceutically acceptable salt thereof in the preparation of drugs for treating a subject with a cancer that is deficient in Homologous Recombination (HR) dependent DNA double strand break (DSB) repair is provided.

In the seventh aspect of the present invention, use of the pharmaceutical composition in the preparation of drugs for treating a subject with a cancer that is deficient in Homologous Recombination (HR) dependent DNA double strand break (DSB) repair is provided.

Preferably, the cancer is deficient in Homologous Recombination (HR) dependent DNA double strand break (DSB) repair.

Preferably, the cancer comprises one or more cancer cells having a reduced or abrogated ability to repair DNA DSB by HR relative to normal cells.

Preferably, the cancer has a BRCA-1 or BRCA-2 deficient mutant phenotype. Further preferably, the cancer is a BRCA1 or/and BRCA2 deficient mutant cancer.

Preferably, the cancer is breast, ovary, pancreas, prostate, rectal, colon or breast cancer.

To examine the degree of inhibition of the compounds provided in the present invention on the PARP enzyme, the activity of the compounds of the present invention for PARP enzyme are determined through biological enzyme activity assay.

PARP is an enzyme responsible for post-translational modification, which may be activated by means of DNA damage. The process catalyzed by PARP in vivo is mainly NAD-dependent poly(ADP-ribosyl)ation, in which the substrates are mainly some nuclear proteins including PARP, one example of which is histone. In the present invention, the PARP activity is assayed by determining the poly(ADP-ribosyl)ation degree of histone coated in a 96-well plate in the presence of NAD, and the PARP activity under the action of a PARP inhibitor is correspondingly assayed, thereby evaluating the degree of inhibition of the compounds on PARP activity.

DETAILED DESCRIPTION

Hereinafter, the present invention is further described with reference to examples; however, the scope of the present invention is not limited thereto.

The experimental methods where no specific conditions are given in the examples of the present invention are generally carried out in accordance with conventional conditions, or in accordance with the conditions recommended by the manufacturer of the raw material or the product. The reagents for which no specific sources are noted are conventional reagents commercially available from the market.

The terms used in the description and claims have the following meanings, unless stated otherwise.

In the present invention, the term "$C_1$-$C_6$ alkyl" refers to a saturated linear or branched monovalent hydrocarbyl group having 1 to 6 carbon atoms. Examples include, but are not limited to, methyl, ethyl, propyl, isopropyl, n-butyl, iso-butyl, and t-butyl.

The term "$C_1$-$C_6$ haloalkyl" refers to a saturated linear or branched monovalent hydrocarbyl group having 1 to 6 carbon atoms in which the hydrogen atoms are partially or totally replaced by halogen atoms.

The term "$C_1$-$C_6$ alkoxy" refers to a saturated linear or branched monovalent hydrocarbyl group having 1 to 6 carbon atoms oxygen to which an oxygen atom is attached. Examples include, but are not limited to, methoxy, ethoxy, propoxy, isopropoxy, n-butoxy, iso-butoxy, and t-butoxy.

The term "enantiomer" refers to stereoisomers that are mirror images of each other.

The term "diastereomer" refers to stereoisomers having two or more chiral centers in their molecules that are not mirror images of each other.

The term "conformational isomer" refers to an isomer produced by the rotation of a single bond of an organic molecule.

The term "tautomer" refers to the phenomenon that the structure of a certain organic compound is interconverted between two balanced functional isomers, and the corresponding isomers are referred to as tautomers.

The term "mesomer" refers to a non-optically active compound that contains an asymmetric atom in the molecule that is symmetrically formed.

The term "racemate" refers to an equimolar mixture of an optically active chiral molecule with its enantiomer.

The term "metabolite and metabolite precursor or prodrug" refers to a substance produced or consumed by a metabolic process. The prodrug refers to a compound obtained by chemical modification of a drug, which is not active in vitro and has a pharmacodynamic effect in an organism or human by converting into the original drug.

The term "derivative" refers to a complex product derived from the substitution of an atom or group in a compound with an additional atom or group.

The term "therapeutically acceptable amount" any amount that achieves the desired biological response.

The term "halogen" and "halo" refer to F, Cl, Br, and I.

"Pharmaceutical composition" refers to a mixture of one or more of the compound according to the present invention or a pharmaceutically acceptable salt, solvate, hydrate or prodrug thereof with other chemical ingredients, for example, a pharmaceutically acceptable carrier. The pharmaceutical composition is provided for the purpose of promoting the administration of the drug to an animal.

"Pharmaceutically acceptable carrier" refers to an inactive ingredient in the pharmaceutical composition that does not cause significant irritation to an organism and does not interfere with the biological activity and properties of the administered compound, for example, but not limited to: calcium carbonate, calcium phosphate, various carbohydrates (e.g. lactose, and mannitol), starch, cyclodextrin, magnesium stearate, cellulose, magnesium carbonate, acrylic polymers or methacrylic polymers, gel, water, polyethylene glycol, propylene glycol, ethylene glycol, castor oil, hydrogenated castor oil or polyethoxyhydrogenated castor oil, sesame oil, corn oil, and peanut oil.

In addition to the pharmaceutically acceptable carrier, the pharmaceutical composition may further comprises pharmaceutically acceptable adjuvants, for example antibacterial agents, antifungal agents, antimicrobial agents, preservatives, colorants, solubilizers, thickeners, surfactants, chelating agents, proteins, amino acids, lipids, carbohydrates, vitamins, minerals, trace elements, sweeteners, pigments, fragrances or a combination thereof.

In the present invention, a compound and use of the compound as a poly(ADP-ribose) polymerase inhibitor are provided. The process parameters may be appropriately adapted by those skilled in the art based on the disclosures herein. It should be particularly noted that all equivalent replacements and modifications are apparent to those skilled in the art, and contemplated by the present invention. The method and use of the present invention have been described with reference to preferred examples, and it is apparent that the invention may be implemented and applied by persons of skill in the art through modification, or appropriate alternation and combination made to the method and use of the present invention without departing from the disclosures, spirits and scope of the present invention.

Hereinafter, the present invention is further described with reference to examples.

PREPARATION EXAMPLES

The structure of the compound is determined by nuclear magnetic resonance (NMR) or/and mass spectrometry (MS). The NMR shift (δ) is given in $10^{-6}$ (ppm). During the determination, the solvent is deuterated methanol, deuterated dimethyl sulfoxide, deuterated chloroform, and the internal standard is tetramethylsilane.

For the determination by MS, LC-MS (manufacturer: Shimadzu, model: LCMS-2020) is employed.

The known starting materials in the present invention may be synthesized by or in accordance with methods known in the art, or commercially available from the market.

Example 1

Preparation of Compound (1): 4-(3-(4-(1H[1,2,3]triazolo[4,5-b]pyridin-5-yl)piperazine-1-carbonyl)-4-fluorobenzyl)phthalazin-1(2H)-one The reaction scheme was specifically as follows.

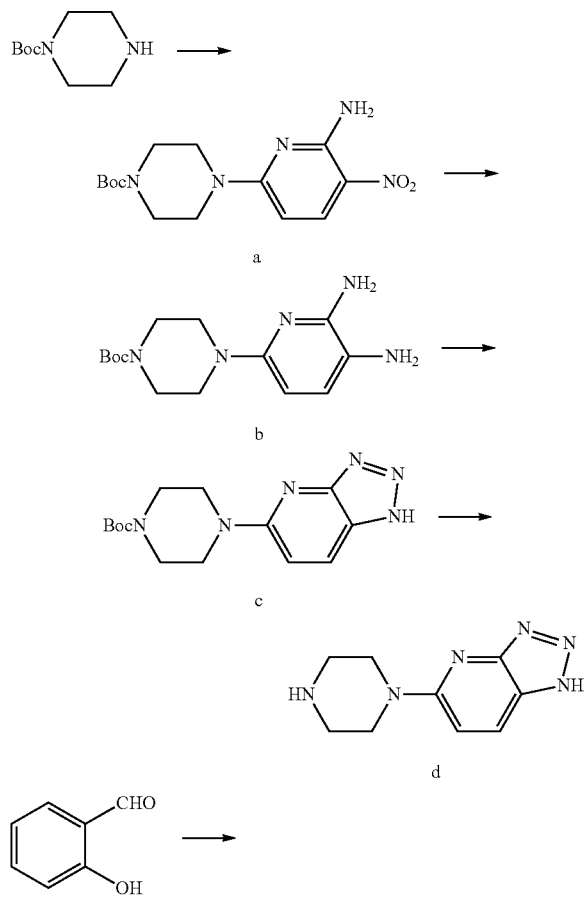

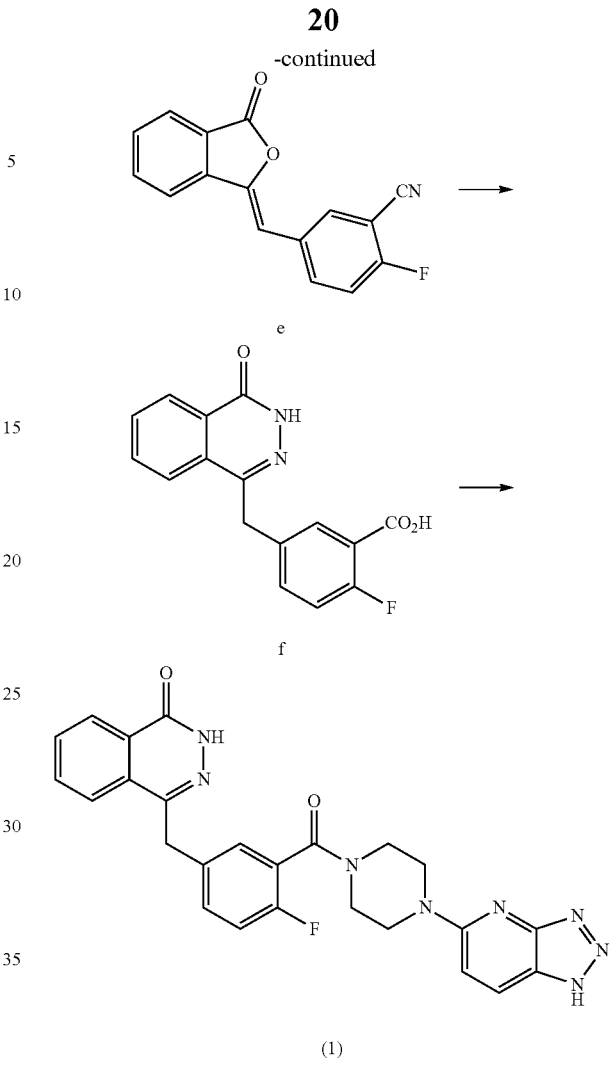

Step 1: Preparation of t-butyl 4-(6-amino-5-nitropyridin-2-yl)piperazine-1-carbonate To a compound mono-t-butoxycarbonyl (mono-t-Boc) protected piperazine (1.86 g, 10 mmol) dissolved in dimethyl formamide (10 mL), 6-chloro-3-nitro-2-aminopyridine (1.91 g, 11 mmol) and diisopropylethyl amine (1.55 g, 12 mmol) were added, and reacted for 8 hrs at room temperature. Then, the solvent was removed under reduced pressure, and the residue was separated by flash column chromatography (dichloromethane:methanol=50:1), to obtain Compound a: t-butyl 4-(6-amino-5-nitropiperidin-2-yl)piperazine-1-carbonate as a white solid (2.72 g, yield 84%). MS (ESI) m/z: [M+H]$^+$=324.

Step 2: Preparation of t-butyl 4-(5,6-diaminopyridin-2-yl)piperazine-1-carbonate 10% palladium on carbon (259 mg) was added to a solution of Compound a (2.59 g, 8 mmol) in methanol (20 mL), hydrogenated for 7 hrs at room temperature, and filtered. The residue was separated by flash column chromatography (dichloromethane:methanol=10:1), to obtain Compound b: t-butyl 4-(5,6-diaminopiperidin-2-yl)piperazine-1-carbonate as a yellow solid (2.25 g, yield 93%). MS (ESI) m/z: [M+H]$^+$=294.

Step 3: Preparation of t-butyl 4-(1H-[1,2,3]triazolo [4,5-b]pyridin-5-yl)piperazine-1-carbonate To a solution of Compound b (1.76 g, 6 mmol) dissolved in acetic acid (30 mL), sodium nitrite (0.42 g, 6 mmol) was added, heated to reflux, reacted for 8 hrs and then cooled. The solvent was removed under reduced pressure, and the residue was separated by flash column chromatography (dichloromethane:methanol=10:1), to obtain Compound c: t-butyl 4-(1H-[1,2,3]triazolo[4,5-b]pyridin-5-yl)piperazine-1-carbonate as a light yellow solid (1.64 g, yield 90%). MS (ESI) m/z: [M+H]$^+$=305.

Step 4: Preparation of 5-(piperazine-1-yl)-1H-[1,2,3]triazolo[4,5-b]piperidine To a solution of Compound c (1.52 g, 5 mmol) dissolved in dichloromethane (10 mL), trifluoroacetic acid (2.28 g, 20 mmol) was added, and reacted for 8 hrs at room temperature. Then, the solvent was removed under reduced pressure, and the residue was taken up in dichloromethane (20 mL). Sodium bicarbonate was added until the pH was 8. The solvent was removed by concentration, and the residue was separated by flash column chromatography (dichloromethane:methanol=10:1) to obtain Compound d: 5-(piperazine-1-yl)-1H-[1,2,3]triazolo[4,5-b]piperidine as a light yellow solid (0.87 g, yield 86%). MS (ESI) m/z: [M+H]$^+$=205.

Step 5: Preparation of 2-fluoro-4-((3-oxoisobenzofuran-1(3H)-ylidene)methyl)benzonitrile To a solution of sodium methoxide (61.8 g, 1.14 mol) dissolved in anhydrous methanol (1 L) in an ice bath, dimethyl phosphite (97 mL, 1.06 mol) was slowly added. 2-carboxybenzaldehyde (135 g, 0.9 mol) was slowly added dropwise in 20 min such that the temperature of the reaction system was kept below 5° C. The reaction system was gradually heated to room temperature, and methanesulfonic acid (81.6 mL, 1.26 mol) was gradually added dropwise in 0.5 hr. The solvent was removed under reduced pressure, and the residue was diluted in water (600 mL), and extracted with dichloromethane (500 mL×3). The organic phases were combined, extracted with water (100 mL×3), and dried over anhydrous magnesium sulfate. The solvent was removed under reduced pressure to obtain a compound dimethyl 3-oxo-1,3-dihydroisobenzofuran-1-ylphosphite as a light yellow solid, which was directly used in a next reaction without purification. To a solution of the compound dimethyl 3-oxo-1,3-dihydroisobenzofuran-1-ylphosphite (35 g, 0.14 mol) obtained in the previous step without purification dissolved in tetrahydrofuran (330 mL), 2-fluoro-5-formyl benzonitrile (20.9 g, 0.14 mol) was added. The system was cooled to 15° C., and triethylamine (19.5 mL, 0.14 mol) was slowly added dropwise in 30 min. The reaction system was gradually heated to room temperature, the solvent was removed under reduced pressure, and the residue was slurried in water (250 mL), and filtered, to obtain Compound e: 2-fluoro-4-((3-oxoisobenzofuran-1(3H)-ylidene)methyl) benzonitrile as a white solid (37.2 g, yield 96%).

Step 6: Preparation of 2-fluoro-5-((4-oxo-3,4-dihydrophthalazin-1-yl)methyl)benzoic acid To a solution of Compound e (37 g, 0.14 mol) dissolved in water (200 mL), a 13 N sodium hydroxide solution (50 mL) was added, heated to 90° C., and stirred for 1 hr. The reaction system was cooled to 70° C., added with hydrazine hydrate (100 mL, 2 mol), and stirred for 18 hrs while the temperature was maintained. The reaction solution was cooled to room temperature, adjusted to pH 4 with 8 N hydrochloric acid, and filtered. The filter cake was sequentially washed with water (60 mL×2) and then diethyl ether (50 mL×3), and dried under vacuum to obtain Compound f: 2-fluoro-5-((4-oxo-3,4-dihydrophthalazin-1-yl)methyl)benzoic acid as a white solid (30.1 g, yield 77%). MS (ESI) m/z: [M+H]$^+$=299.

Step 7: Preparation of 4-(3-(4-(1H-[1,2,3]triazolo[4,5-b]pyridin-5-yl)piperazine-1-carbonyl)-4-fluorobenzyl)phthalazin-1(2H)-one To a solution of Compound f (50 mg, 0.17 mmol) dissolved in dimethyl formamide (5 mL), Compound d (49 mg, 0.24 mmol), 2-(7-azabenzotriazolyl)-N,N,N',N'-tetramethyluronium hexafluorophosphate (77 mg, 0.2 mmol), and triethylamine (70 mg, 0.7 mmol) were added, and stirred overnight at room temperature. The solvent was removed by concentration, and the residue was separated by flash column chromatography (dichloromethane:methanol=10:1), to obtain Compound (1): 4-(3-(4-(1H-[1,2,3]triazolo[4,5-b]pyridin-5-yl)piperazine-1-carbonyl)-4-fluorobenzyl) phthalazin-1(2H)-one as a white solid (16 mg, yield 20%). MS (ESI) m/z: [M+H]$^+$=485. $^1$NMR (300 MHz, DMSO-d6):

δ 12.57 (s, 1H), 8.24-8.12 (m, 2H), 7.96-7.74 (m, 1H), 7.89-7.81 (m, 3H), 7.43-7.38 (m, 2H), 7.26-7.21 (m, 1H), 7.05-6.99 (m, 1H), 4.32 (s, 2H), 3.73 (br, 6H), 3.57 (br, 2H).

Example 2

Compound (2): Preparation of 4-(4-fluoro-3-(4-(2-methyl-1H-imidazo[4,5-b]pyridin-5-yl)piperazine-1-carbonyl)benzyl)phthalazin-1(2H)-one The reaction scheme was specifically as follows.

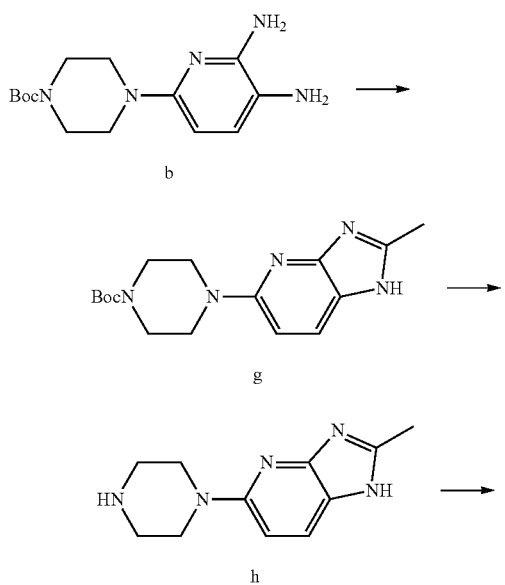

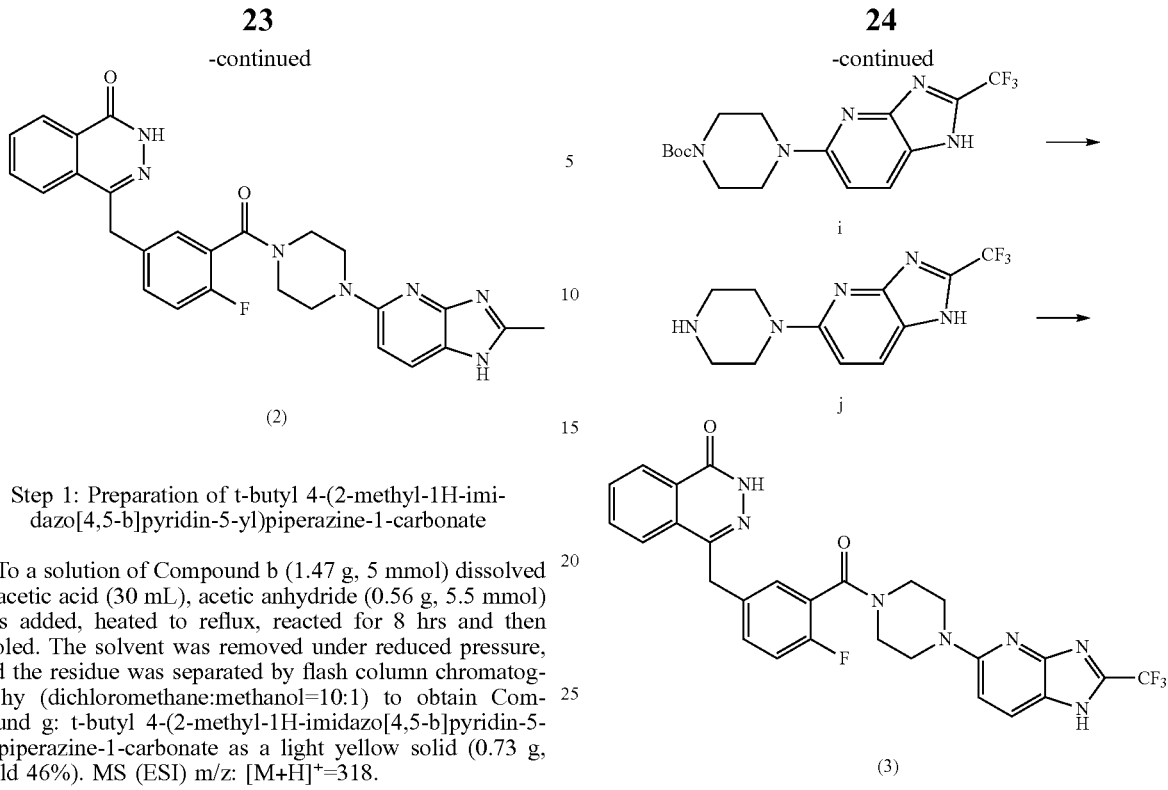

(2)

Step 1: Preparation of t-butyl 4-(2-methyl-1H-imidazo[4,5-b]pyridin-5-yl)piperazine-1-carbonate To a solution of Compound b (1.47 g, 5 mmol) dissolved in acetic acid (30 mL), acetic anhydride (0.56 g, 5.5 mmol) was added, heated to reflux, reacted for 8 hrs and then cooled. The solvent was removed under reduced pressure, and the residue was separated by flash column chromatography (dichloromethane:methanol=10:1) to obtain Compound g: t-butyl 4-(2-methyl-1H-imidazo[4,5-b]pyridin-5-yl)piperazine-1-carbonate as a light yellow solid (0.73 g, yield 46%). MS (ESI) m/z: [M+H]$^+$=318.

Step 2: Preparation of 2-methyl-5-(piperazine-1-yl)-1H-imidazo[4,5-b]pyridine

Analogous to the process for preparing Compound d in Step 4 in Example 1, Compound g is deprotected by reacting with trifluoroacetic acid to produce Compound h: 2-methyl-5-(piperazine-1-yl)-1H-imidazo[4,5-b]pyridine (320 mg, yield 82%). MS (ESI) m/z: [M+H]$^+$=218.

Step 3: Preparation of 4-(4-fluoro-3-(4-(2-methyl-1H-imidazo[4,5-b]pyridin-5-yl)piperazine-1-carbonyl)benzyl)phthalazin-1(2H)-one Analogous to the process for preparing Compound (1) in Step 7 in Example 1, Compound h was condensed with Compound f to produce Compound (2): 4-(4-fluoro-3-(4-(2-methyl-1H-imidazo[4,5-b]pyridin-5-yl)piperazine-1-carbonyl)benzyl)phthalazin-1(2H)-one (26 mg, yield 32%). MS (ESI) m/z: [M+H]$^+$=498. $^1$HNMR (300 MHz DMSO-d6): δ 12.55 (s, 1H), 8.23-8.12 (m, 2H), 7.96-7.75 (m, 1H), 7.89-7.80 (m, 3H), 7.44-7.38 (m, 2H), 7.27-7.22 (m, 1H), 7.06-6.98 (m, 1H), 4.33 (s, 2H), 3.72 (br, 4H), 3.56 (br, 4H), 2.63 (s, 3H).

Example 3

Compound (3): Preparation of 4-(4-fluoro-3-(4-(2-trifluoromethyl)-1H-imidazo[4,5-b]pyridin-5-yl)piperazine-1-carbonyl)benzyl)phthalazin-1(2H)-one The reaction scheme was specifically as follows.

Step 1: Preparation of t-butyl 4-(2-trifluoromethyl-1H-imidazo[4,5-b]pyridin-5-yl)piperazine-1-carbonate To a solution of Compound b (1.47 g, 5 mmol) dissolved in trifluoroacetic acid (30 mL), trifluoroacetic anhydride (1.16 g, 5.5 mmol) was added, heated to reflux, reacted for 8 hrs and then cooled. The solvent was removed under reduced pressure, and the residue was separated by flash column chromatography (dichloromethane:methanol=10:1) to obtain Compound 1: t-butyl 4-(2-trifluoromethyl-1H-imidazo[4,5-b]pyridin-5-yl)piperazine-1-carbonate as a light yellow solid (0.69 g, yield 37%). MS (ESI) m/z: [M+H]$^+$=372.

Step 2: Preparation of 5-(piperazine-1-yl)-2-trifluoromethyl-1H-imidazo[4,5-b]pyridine Analogous to the process for preparing Compound d in Step 4 in Example 1, Compound i was deprotected by reacting with trifluoroacetic acid to produce Compound j: 5-(piperazine-1-yl)-2-trifluoromethyl-1H-imidazo[4,5-b]pyridine (269 mg, yield 78%). MS (ESI) m/z: [M+H]$^+$=272.

Step 3: Preparation of 4-(4-fluoro-3-(4-(2-trifluoromethyl)-1H-imidazo[4,5-b]pyridin-5-yl)piperazine-1-carbonyl)benzyl)phthalazin-1(2H)-one Analogous to the process for preparing Compound (1) in Step 7 in Example 1, Compound j was condensed with Compound f to produce Compound (3): 4-(4-fluoro-3-(4-(2-methyl-1H-imidazo[4,5-b]pyridin-5-yl)piperazine-1-carbonyl)benzyl)phthalazin-1(2H)-one (38 mg, yield 41%). MS (ESI) m/z: [M+H]$^+$=552. $^1$HNMR (300 MHz, DMSO-d6): δ 12.59 (br, 1H), 8.25 (d, 1H, J=8.1 Hz), 7.98-7.89 (m, 3H), 7.87-7.80 (m, 2H), 7.45-7.38 (m, 2H), 7.26-7.20 (m, 1H), 6.92 (d, 1H, J=9.0 Hz), 4.33 (s, 2H), 3.73 (br, 2H), 3.63 (br, 2H), 3.46 (br, 4H).

Example 4

Compound (4): Preparation of 4-(3-(4-(1H-imidazo[4,5-b]pyridin-5-yl)piperazine-1-carbonyl)-4-fluorobenzyl)phthalazin-1(2H)-one The reaction scheme was specifically as follows.

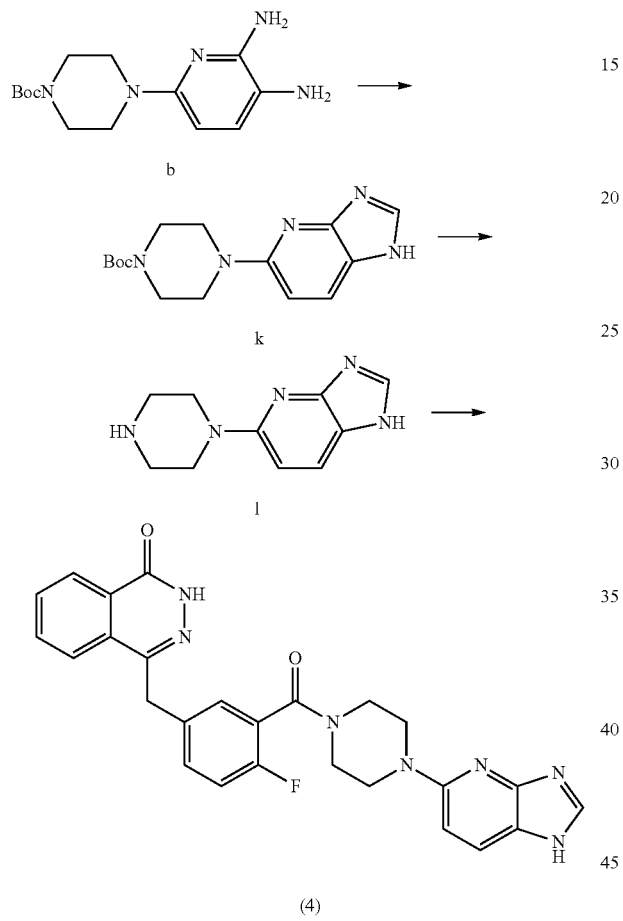

(4)

Step 1: Preparation of t-butyl 4-(1H-imidazo[4,5-b]pyridin-5-yl)piperazine-1-carbonate To a solution of Compound b (1.47 g, 5 mmol) dissolved in trimethyl orthoformate (6 g), p-toluene sulfonic acid (86 mg, 0.5 mmol) was added, heated to reflux, reacted for 8 hrs and then cooled. The solvent was removed under reduced pressure, and the residue was separated by flash column chromatography (dichloromethane:methanol=10:1) to obtain Compound k: t-butyl 4-(1H-imidazo[4,5-b]pyridin-5-yl)piperazine-1-carbonate as a light yellow solid (0.73 g, yield 48%). MS (ESI) m/z: [M+H]$^+$=304.

Step 2: Preparation of 5-(piperazine-1-yl)-1H-imidazo[4,5-b]pyridine

Analogous to the process for preparing Compound d in Step 4 in Example 1, Compound k was deprotected by reacting with trifluoroacetic acid to produce Compound 1: 5-(piperazine-1-yl)-1H-imidazo[4,5-b]pyridine (307 mg, yield 73%). MS (ESI) m/z: [M+H]$^+$=204.

Step 3: Preparation of 4-(3-(4-(1H-imidazo[4,5-b]pyridin-5-yl)piperazine-1-carbonyl)-4-fluorobenzyl)phthalazin-1(2H)-one Analogous to the process for preparing Compound (1) in Step 7 in Example 1, Compound 1 was condensed with Compound f to produce Compound (4): 4-(3-(4-(1H-imidazo[4,5-b]pyridin-5-yl)piperazine-1-carbonyl)-4-fluorobenzyl)phthalazin-1(2H)-one (25 mg, yield 31%). MS (ESI) m/z: [M+H]$^+$=484. $^1$HNMR (300 MHz, DMSO-d6): δ 12.61 (br, 1H), 8.27-8.24 (m, 1H), 8.16 (s, 1H), 8.00-7.97 (m, 1H), 7.93-7.82 (m, 4H), 7.45-7.39 (m, 2H), 7.28-7.22 (m, 1H), 6.83-6.80 (m, 1H), 4.34 (s, 2H), 3.73 (br, 2H), 3.58 (br, 2H), 3.42 (br, 4H).

Example 5

Compound (5): Preparation of 4-(4-fluoro-3-(4-(2-oxo-2,3-dihydro-1H-imidazo[4,5-b]pyridin-5-yl)piperazine-1-carbonyl) benzyl)phthalazin-1(2H)-one The reaction scheme was specifically as follows.

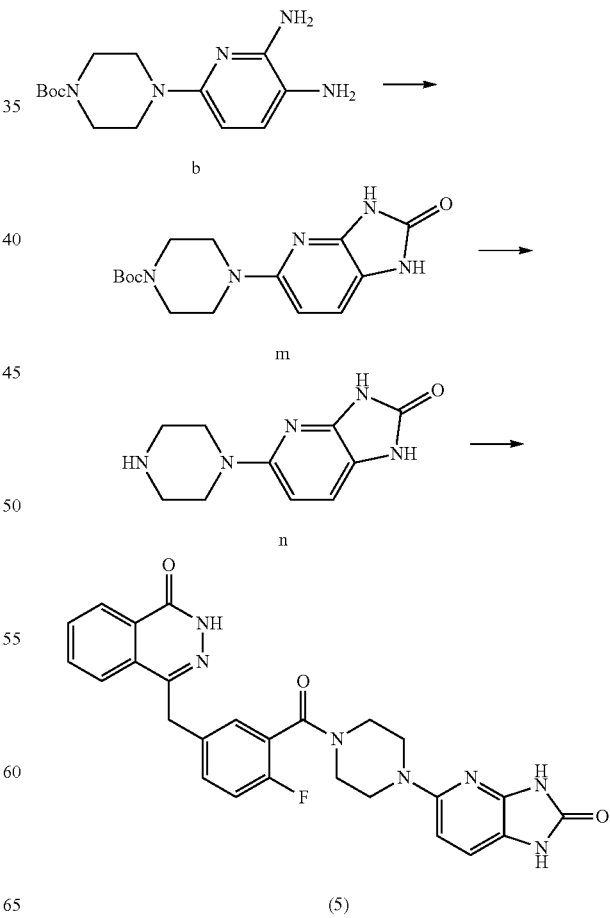

(5)

Step 1: Preparation of t-butyl 4-(2-oxo-2,3-dihydro-1H-imidazo[4,5-b]pyridin-5-yl)piperazine-1-carbonate To a solution of Compound b (1.47 g, 5 mmol) dissolved in anhydrous tetrahydrofuran (20 mL), carbonyl diimidazole (1.62 g, 10 mmol) was added, heated to reflux, reacted for 8 hrs and then cooled. The solvent was removed under reduced pressure, and the residue was separated by flash column chromatography (dichloromethane:methanol=10:1) to obtain Compound m: t-butyl 4-(2-oxo-2,3-dihydro-1H-imidazo[4,5-b]pyridin-5-yl)piperazine-1-carbonate as a light yellow solid (1.24 g, yield 78%). MS (ESI) m/z: $[M+H]^+=320$.

Step 2: Preparation of 5-(piperazine-1-yl)-1H-imidazo[4,5-b]pyridin-2(3H)-one Analogous to the process for preparing Compound d in Step 4 in Example 1, Compound m was deprotected by reacting with trifluoroacetic acid to produce Compound n: 5-(piperazine-1-yl)-1H-imidazo[4,5-b]pyridin-2(3H)-one (331 mg, yield 79%). MS (ESI) m/z: $[M+H]^+=220$.

Step 3: Preparation of 4-(4-fluoro-3-(4-(2-oxo-2,3-dihydro-1H-imidazo[4,5-b]pyridin-5-yl)piperazine-1-carbonyl) benzyl)phthalazin-1(2H)-one Analogous to the process for preparing Compound (1) in Step 7 in Example 1, Compound n was condensed with Compound f to produce Compound (5): 4-(4-fluoro-3-(4-(2-oxo-2,3-dihydro-1H-imidazo[4,5-b]pyridin-5-yl)piperazine-1-carbonyl) benzyl)phthalazin-1(2H)-one (32 mg, yield 36%). MS (ESI) m/z: $[M+H]^+=500$.

$^1$HNMR (300 MHz, DMSO-d6): δ 12.58 (br, 1H), 10.97 (br, 1H), 10.39 (br, 1H), 8.28-8.26 (m, 1H), 7.99-7.96 (m, 1H), 7.92-7.81 (m, 2H), 7.46-7.42 (m, 1H), 7.39-7.37 (m, 1H), 7.27-7.20 (m, 1H), 7.11 (d, 1H, J=8.4 Hz), 6.36 (d, 1H, J=8.4 Hz), 4.33 (s, 2H), 3.73 (br, 2H), 3.40 (br, 2H), 3.26-3.21 (br, 4H).

Example 6

Compound (6): Preparation of 4-(3-(4-(3H-imidazo[4,5-c]pyridin-6-yl)piperazine-1-carbonyl)-4-fluorobenzyl)phthalazin-1(2H)-one The reaction scheme was specifically as follows.

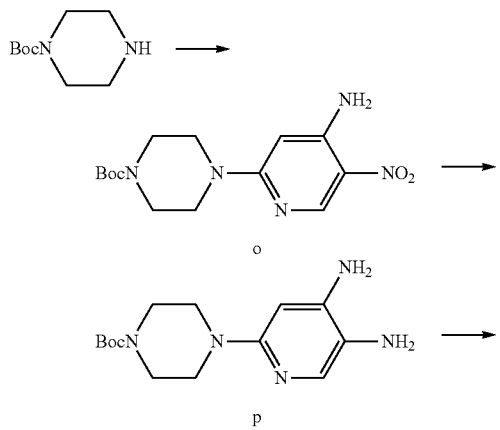

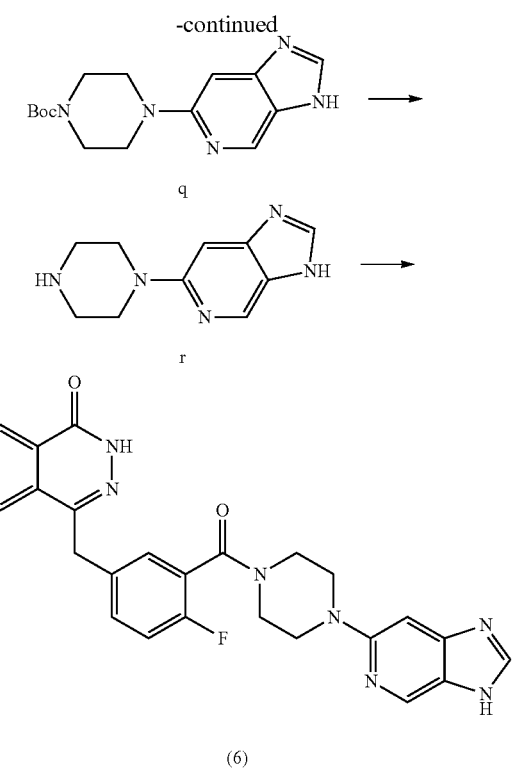

(6)

Step 1: Preparation of t-butyl 4-(4-amino-5-nitropiperidin-2-yl)piperazine-1-carbonate Analogous to the process for preparing Compound a in Step 1 in Example 1, a compound mono-t-butoxycarbonyl (mono-t-Boc) protected piperazine was subjected to nucleophilic substitution with 2-chloro-5-nitro-4-aminopyridine, to produce Compound o:
t-butyl 4-(4-amino-5-nitropiperidin-2-yl)piperazine-1-carbonate (1.1 g, yield 86%). MS (ESI) m/z: $[M+H]^+=324$.

Step 2: Preparation of t-butyl 4-(4,5-diaminopiperidin-2-yl)piperazine-1-carbonate Analogous to the process for preparing Compound b in Step 2 in Example 1, Compound o was catalytically hydrogenated to produce Compound p: t-butyl 4-(4,5-diaminopiperidin-2-yl)piperazine-1-carbonate (0.9 g, yield 97%). MS (ESI) m/z: $[M+H]^+=294$.

Step 3: Preparation of t-butyl 4-(3H-imidazo[4,5-c]pyridin-6-yl)piperazine-1-carbonate Analogous to the process for preparing Compound k in Step 1 in Example 4, Compound p was cyclized with trimethyl orthoformate to produce Compound q: t-butyl 4-(3H-imidazo[4,5-c]pyridin-6-yl)piperazine-1-carbonate (0.6 g, yield 82%). MS (ESI) m/z: $[M+H]^+=304$.

Step 4: Preparation of 6-(piperazine-1-yl)-3H-imidazo[4,5-c]pyridine

Analogous to the process for preparing Compound d in Step 4 in Example 1, Compound q was deprotected by reacting with trifluoroacetic acid to produce Compound r:

6-(piperazine-1-yl)-3H-imidazo[4,5-c]pyridine (279 mg, yield 75%). MS (ESI) m/z: [M+H]+=204.

Step 5: Preparation of 4-(3-(4-(3H-imidazo[4,5-c]pyridin-6-yl)piperazine-1-carbonyl)-4-fluorobenzyl)phthalazin-1(2H)-one Analogous to the process for preparing Compound (1) in Step 7 in Example 1, Compound r was condensed with Compound f to produce Compound (6): 4-(3-(4-(3H-imidazo[4,5-c]pyridin-6-yl)piperazine-1-carbonyl)-4-fluorobenzyl)phthalazin-1(2H)-one (16 mg, yield 20%). MS (ESI) m/z: [M+H]+=484. ¹HNMR (300 MHz, DMSO-d6): δ 12.57 (s, 1H), 12.35 (s, 1H), 8.54 (s, 1H), 8.25 (d, 1H, J=7.8 Hz), 8.09 (s, 1H), 7.98-7.80 (m, 3H), 7.42-7.37 (m, 2H), 7.26-7.20 (m, 2H), 6.76 (s, 1H), 4.33 (s, 2H), 3.75 (br, 2H), 3.50 (br, 2H), 3.39 (br, 4H).

Example 7

Compound (7): Preparation of 4-(3-(4-(3H-imidazo[4,5-b]pyridin-6-yl)piperazine-1-carbonyl)-4-fluorobenzyl)phthalazin-1(2H)-one The reaction scheme was specifically as follows.

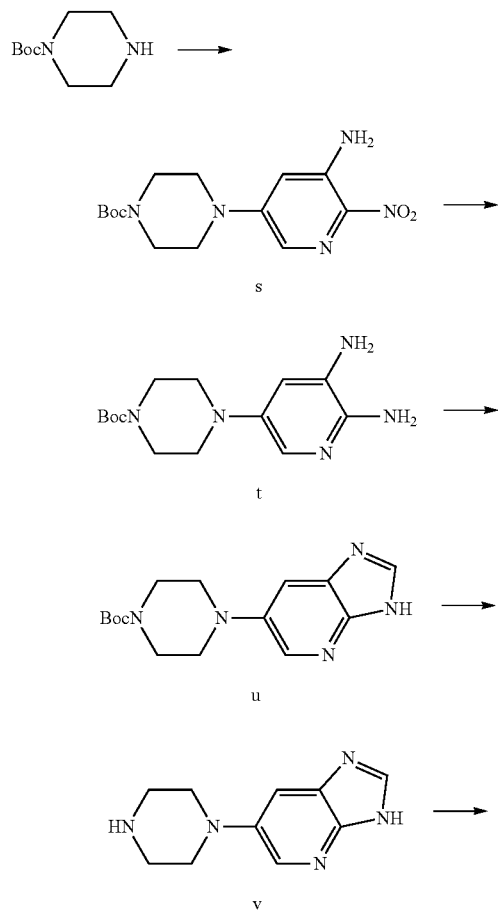

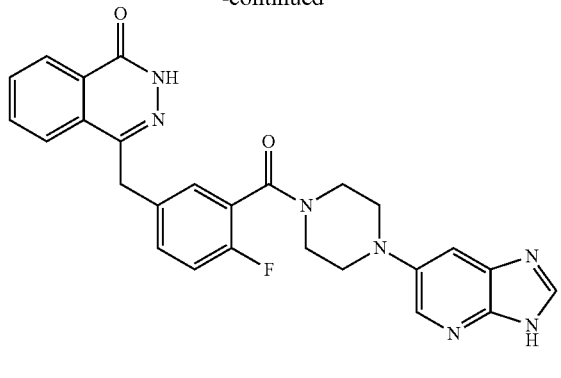

(7)

Step 1: Preparation of t-butyl 4-(5-amino-6-nitropiperidin-3-yl)piperazine-1-carbonate Analogous to the process for preparing Compound a in Step 1 in Example 1, a compound mono-t-butoxycarbonyl (mono-t-Boc) protected piperazine was subjected to nucleophilic substitution with 5-bromo-2-nitro-3-aminopyridine to obtain Compound s: t-butyl 4-(5-amino-6-nitropiperidin-3-yl)piperazine-1-carbonate (0.7 g, yield 82%). MS (ESI) m/z: [M+H]+=324.

Step 2: Preparation of t-butyl 4-(5,6-diaminopiperidin-3-yl)piperazine-1-carbonate Analogous to the process for preparing Compound b in Step 2 in Example 1, Compound s was catalytically hydrogenated to obtain Compound t: t-butyl 4-(5,6-diaminopiperidin-3-yl)piperazine-1-carbonate (0.52 g, yield 91%). MS (ESI) m/z: [M+H]+=294.

Step 3: Preparation of t-butyl 4-(3H-imidazo[4,5-b]pyridin-6-yl)piperazine-1-carbonate Analogous to the process for preparing Compound k in Step 1 in Example 4, Compound t was cyclized with trimethyl orthoformate to produce Compound u: t-butyl 4-(3H-imidazo[4,5-b]pyridin-6-yl)piperazine-1-carbonate (0.36 g, yield 73%). MS (ESI) m/z: [M+H]+=304.

Step 4: Preparation of 6-(piperazine-1-yl)-3H-imidazo[4,5-b]pyridine

Analogous to the process for preparing Compound d in Step 4 in Example 1, Compound u was deprotected by reacting with trifluoroacetic acid to produce Compound v: 6-(piperazine-1-yl)-3H-imidazo[4,5-b]pyridine (126 mg, yield 82%). MS (ESI) m/z: [M+H]+=204.

Step 5: Preparation of 4-(3-(4-(3H-imidazo[4,5-b]pyridin-6-yl)piperazine-1-carbonyl)-4-fluorobenzyl)phthalazin-1(2H)-one Analogous to the process for preparing Compound (1) in Step 7 in Example 1, Compound v was condensed with Compound f to produce Compound (7): 4-(3-(4-(3H-imidazo[4,5-b]pyridin-6-yl)piperazine-1-carbonyl)-4-fluorobenzyl)phthalazin-1(2H)-one (16 mg, yield 22%). MS (ESI): m/z 484 [M+1]+. NMR (300 MHz, DMSO-d6): δ 12.59 (s, 1H), 8.25-8.20 (m, 3H), 7.98-7.79 (m, 3H), 7.51-

7.45 (m, 1H), 7.42-7.37 (m, 3H), 7.26-7.20 (m, 1H), 4.33 (s, 2H), 3.78 (br, 2H), 3.55-3.47 (m, 2H), 3.19-3.14 (m, 2H), 3.03 (br, 2H).

Example 8

Compound (8): Preparation of 4-(3-(4-(7H-purin-2-yl)piperazine-1-carbonyl)-4-fluorobenzyl)phthalazin-1(2H)-one The reaction scheme was specifically as follows.

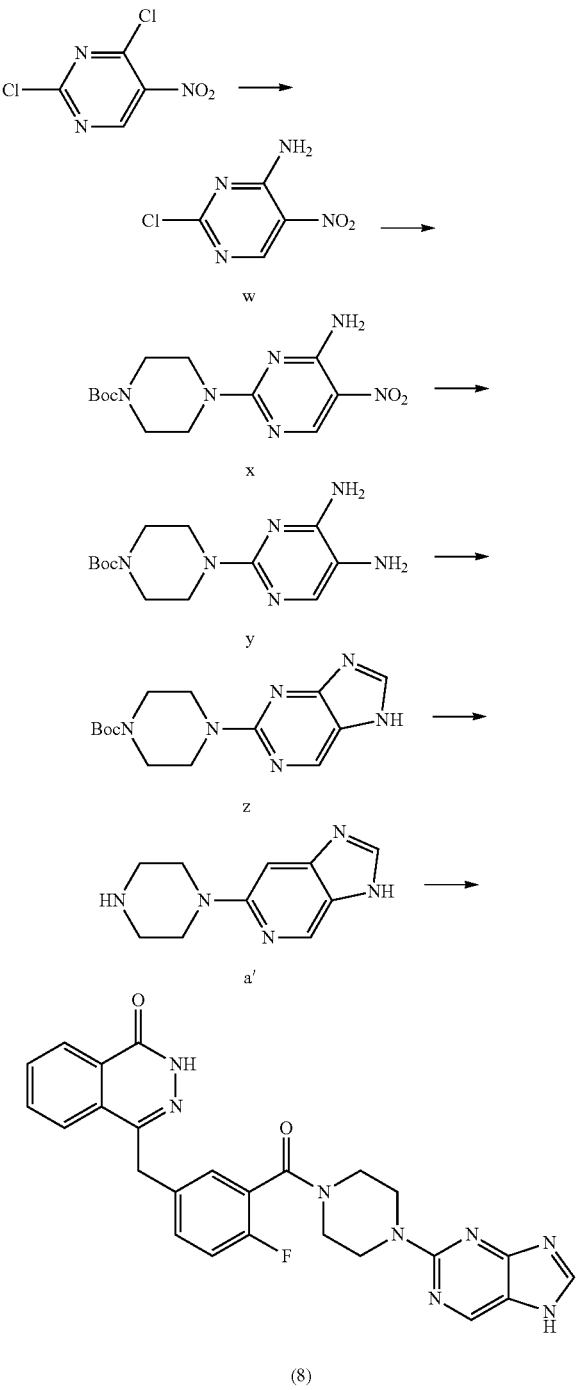

Step 1: Preparation of 2-chloro-5-nitro-4-aminopyrimidine

To 2,4-dichloro-5-nitropyrimidine (500 mg, 2.5 mmol) dissolved in tetrahydrofuran (10 mL), sodium hydroxide (238 mg, 2.8 mmol) and aqueous ammonia (0.3 mL) was added, and reacted for 2 hrs at 55° C. The solvent was removed under reduced pressure, and the residue was separated by flash column chromatography (dichloromethane:methanol=100:1), to obtain Compound w: 2-chloro-5-nitro-4-aminopyrimidine as a white solid (0.47 g, yield 84%). MS (ESI) m/z: [M+H]$^+$=175.

Step 2: Preparation of t-butyl 4-(4-amino-5-nitropyrimidine-2-yl)piperazine-1-carbonate Analogous to the process for preparing Compound a in Step 1 in Example 1, a compound mono-t-butoxycarbonyl (mono-t-Boc) protected piperazine was subjected to nucleophilic substitution with Compound w to produce Compound x: t-butyl 4-(4-amino-5-nitropyrimidine-2-yl)piperazine-1-carbonate (0.61 g, yield 87%). MS (ESI) m/z: [M+H]$^+$=325.

Step 3: Preparation of t-butyl 4-(4,5-diaminopiperidin-2-yl)piperazine-1-carbonate Analogous to the process for preparing Compound b in Step 2 in Example 1, Compound x was catalytically hydrogenated to obtain Compound z: t-butyl 4-(4,5-diaminopiperidin-2-yl)piperazine-1-carbonate (0.26 g, yield 76%). MS (ESI) m/z: [M+H]$^+$=295.

Step 4: Preparation of t-butyl 4-(7H-purin-2-yl)piperazine-1-carbonate

Analogous to the process for preparing Compound k in Step 1 in Example 4, Compound y was cyclized with trimethyl orthoformate to produce Compound z: t-butyl 4-(3H-imidazo[4,5-b]pyridin-6-yl)piperazine-1-carbonate (0.36 g, yield 73%). MS (ESI) m/z: [M+H]$^+$=305.

Step 5: Preparation of 2-(piperazine-1-yl)-7H-purine

Analogous to the process for preparing Compound d in Step 4 in Example 1, Compound z was deprotected by reacting with trifluoroacetic acid to produce Compound a': 2-(piperazine-1-yl)-7H-purine (141 mg, yield 74%). MS (ESI) m/z: [M+H]$^+$=205.

Step 6: Preparation of 4-(3-(4-(7H-purin-2-yl)piperazine-1-carbonyl>4-fluorobenzyl)phthalazin-1(2H)-one Analogous to the process for preparing Compound (1) in Step 7 in Example 1, Compound a' was condensed with Compound f to produce Compound (8): 4-(3-(4-(7H-purin-2-yl)piperazine-1-carbonyl)-4-fluorobenzyl)phthalazin-1(2H)-one (88 mg, yield 74%). MS (ESI) m/z: 485 [M+1]+. $^1$HNMR (300 MHz, DMSO-d6): δ 12.78 (s, 1H), 12.57 (s, 1H), 8.72 (s, 1H), 8.26-8.24 (m, 1H), 8.12 (s, 1H), 7.98-7.96 (m, 1H), 7.91-7.87 (m, 1H), 7.84-7.80 (m, 1H), 7.45-7.41 (m, 1H), 7.39-7.37 (m, 1H), 7.25-7.21 (m, 1H), 4.32 (s, 2H), 3.81-3.79 (m, 2H), 3.72-3.65 (m, 4H), 3.28-3.26 (m, 2H).

Example 9

Compound (9): Preparation of 4-(3-(4-(2-carbonyl-2,3-dihydro-1H-imidazo[4,5-b]pyridin-5-yl)piperazine-1-carbonyl)benzyl)phthalazin-1(2H)-one The reaction scheme was specifically as follows.

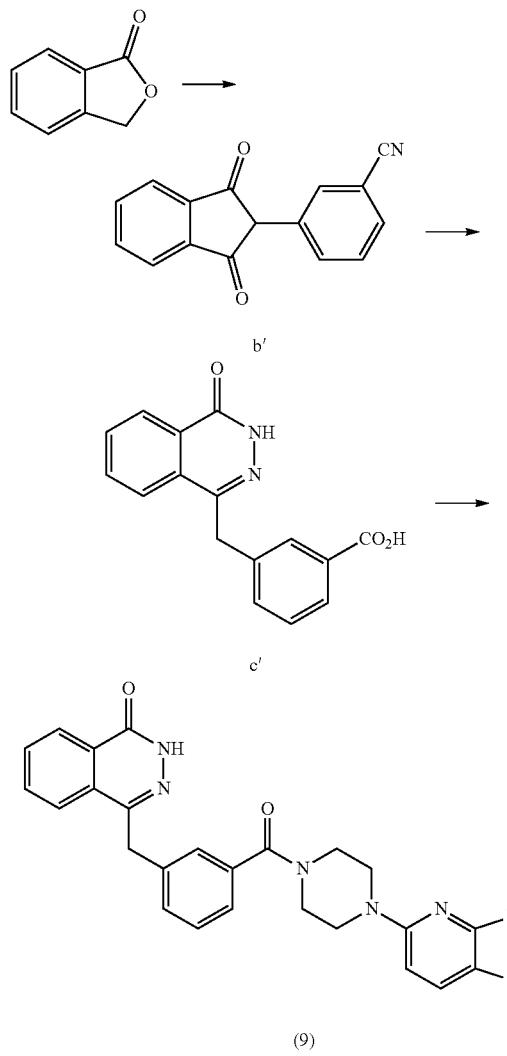

Step 1: Preparation of 3-(1,3-dioxo-2,3-dihydro-1H-inden-2-yl)benzonitrile

To a solution of isobenzofuran-1(3H)-one (51 g, 0.38 mol) and tricyanobenzaldehyde (52 g, 0.39 mol) dissolved in ethyl propionate (200 mL) in an ice bath, a 25% solution (320 mL) of sodium methoxide in methanol was slowly added in 40 min, such that the temperature of the reaction system was maintained below 30° C. The reaction system was gradually warmed to room temperature and heated to reflux for 1 hr. Methanol (100 mL) was continuously added and stirred for 1 hr under reflux. The reaction system was cooled to room temperature and the solvent was removed under reduced pressure. Then, the residue was diluted in water (1 L) and filtered. The filter cake was washed with diethyl ether (200 mL×3), acidified with acetic acid (110 mL), and filtered. The filter cake was washed with water (100 mL), to obtain Compound b': 3-(1,3-dioxo-2,3-dihydro-1H-inden-2-yl)benzonitrile as a red solid (69 g, yield 94%).

Step 2: Preparation of 3-((4-oxo-3,4-dihydrophthalazin-1-yl)methyl)benzoic acid

Analogous to the process for preparing Compound f in Step 6 in Example 1, Compound b was hydrolyzed to produce Compound c': 3-((4-oxo-3,4-dihydrophthalazin-1-yl)methyl)benzoic acid (28 g, yield 55%). MS (ESI) m/z: 281 [M+1]$^+$.

Step 3: Preparation of 4-(3-(4-(2-carbonyl-2,3-dihydro-1H-imidazo[4,5-b]pyridin-5-yl)piperazine-1-carbonyl)benzyl)phthalazin-1(2H)-one Analogous to the process for preparing Compound (1) in Step 7 in Example 1, Compound c' was condensed with Compound n to produce Compound (9): 4-(3-(4-(2-carbonyl-2,3-dihydro-1H-imidazo[4,5-b]pyridin-5-yl)piperazine-1-carbonyl)benzyl)phthalazin-1(2H)-one (37 mg, yield 46%). MS (ESI) m/z: 482 [M+1]$^+$. $^1$HNMR (300 MHz, DMSO-d6): δ 12.58 (br, 1H), 10.95 (br, 1H), 10.37 (br, 1H), 8.27-8.24 (m, 1H), 7.97-7.80 (m, 3H), 7.42-7.35 (m, 3H), 7.26-7.23 (m, 1H), 7.11-7.09 (m, 1H), 6.34 (d, 1H, J=8.7 Hz), 4.35 (s, 2H), 3.69-3.47 (m, 4H), 3.24-3.14 (m, 4H).

Example 10

Compound (10): Preparation of 4-(3-(4-(1H-[1,2,3]triazolo[4,5-b]pyridin-5-yl)piperazine-1-carbonyl)-benzyl)phthalazin-1 (2H)-one The reaction scheme was specifically as follows.

(10)

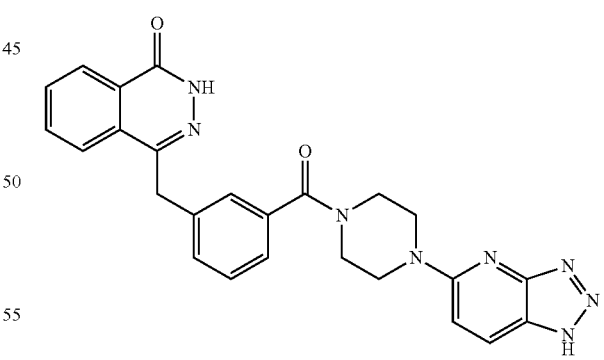

Analogous to the process for preparing Compound (1) in Step 7 in Example 1, Compound c' was condensed with Compound d to produce Compound (10): 4-(3-(4-(1H-[1,2,3]triazolo[4,5-b]pyridin-5-yl)piperazine-1-carbonyl)-benzyl)phthalazin-1 (2H)-one (41 mg, yield 52%). MS (ESI) m/z: 467 [M+1]$^+$. $^1$HNMR (300 MHz, DMSO-d6): δ 12.53 (s, 1H), 8.21-8.10 (m, 2H), 7.93-7.71 (m, 1H), 7.87-7.80 (m, 3H), 7.41-7.35 (m, 3H), 7.24-7.20 (m, 1H), 7.02-6.96 (m, 1H), 4.30 (s, 2H), 3.71 (br, 6H), 3.55 (br, 2H).

Example 11

Compound (11): Preparation of 4-(3-(4-(2-methyl-1H-imidazo[4,5-b]pyridin-5-yl)piperazine-1-carbonyl)benzyl)phthalazin-1(2H)-one The reaction scheme was specifically as follows.

(11)

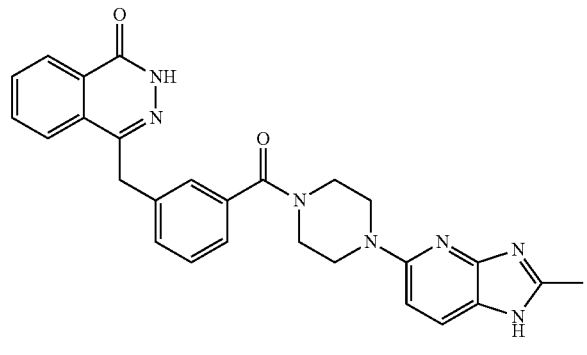

Analogous to the process for preparing Compound (1) in Step 7 in Example 1, Compound c' was condensed with Compound h to produce Compound (11): 4-(3-(4-(2-methyl-1H-imidazo[4,5-b]pyridin-5-yl)piperazine-1-carbonyl)benzyl)phthalazin-1(2H)-one (34 mg, yield 45%). MS (ESI) m/z: 480 [M+1]$^+$. $^1$HNMR (300 MHz, DMSO-d6): δ 12.52 (s, 1H), 8.21-8.10 (m, 2H), 7.94-7.72 (m, 1H), 7.87-7.77 (m, 3H), 7.41-7.34 (m, 3H), 7.26-7.21 (m, 1H), 7.03-6.97 (m, 1H), 4.31 (s, 2H), 3.71 (br, 4H), 3.52 (br, 4H), 2.61 (s, 3H).

Example 12

Compound (12): Preparation of 4-(3-(4-(2-trifluoromethyl)-1H-imidazo[4,5-b]pyridin-5-yl)piperazine-1-carbonyl)benzyl)phthalazin-1(2H)-one The reaction scheme was specifically as follows.

(12)

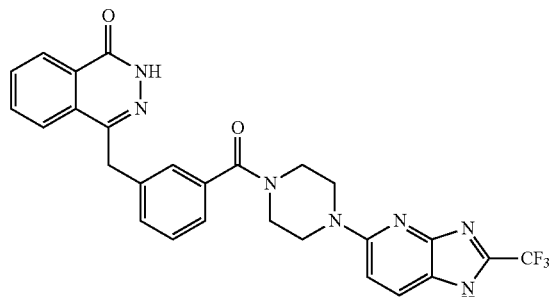

Analogous to the process for preparing Compound (1) in Step 7 in Example 1, Compound c' was condensed with Compound j to produce Compound (12): 4-(3-(4-(2-trifluoromethyl)-1H-imidazo[4,5-b]pyridin-5-yl)piperazine-1-carbonyl)benzyl) phthalazin-1(2H)-one (36 mg, yield 42%). MS (ESI) m/z: 534 [M+1]$^+$. $^1$HNMR (300 MHz, DMSO-d6): δ 12.56 (br, 1H), 8.22 (d, 1H, J=8.1 Hz), 7.95-7.87 (m, 3H), 7.83-7.76 (m, 3H), 7.42-7.36 (m, 2H), 7.22-7.17 (m, 1H), 6.91 (d, 1H, J=9.0 Hz), 4.30 (s, 2H), 3.72 (br, 2H), 3.61 (br, 2H), 3.42 (br, 4H).

Example 13

Compound (13): Preparation of 4-(3-(4-(1H-imidazo[4,5-b]pyridin-5-yl)piperazine-1-carbonyl)benzyl)phthalazin-1(2H)-one The reaction scheme was specifically as follows.

(13)

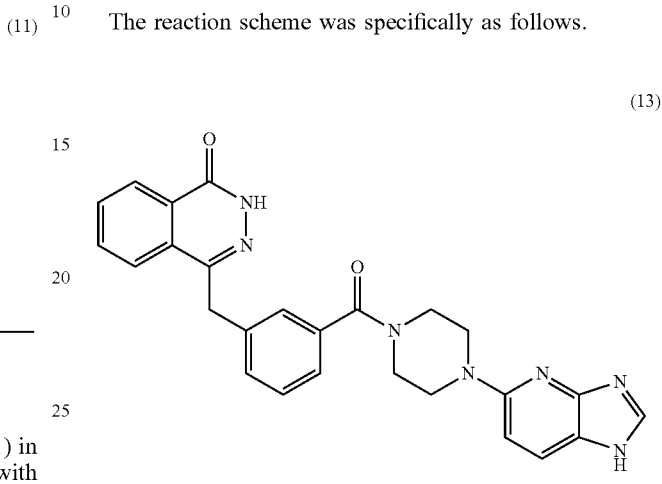

Analogous to the process for preparing Compound (1) in Step 7 in Example 1, Compound c' was condensed with Compound 1 to produce Compound (13): 4-(3-(4-(1H-imidazo[4,5-b]pyridin-5-yl)piperazine-1-carbonyl)benzyl) phthalazin-1(2H)-one (48 mg, yield 58%). MS (ESI) m/z: 466 [M+1]$^+$. $^1$HNMR (300 MHz, DMSO-d6): δ 12.57 (br, 1H), 12.50 (br, 1H), 8.23 (d, 1H, J=7.6 Hz), 8.0 (s, 1H), 7.96-7.93 (m, 1H), 7.88-7.72 (m, 3H), 7.40-7.34 (m, 3H), 7.25-7.24 (m, 1H), 6.79-6.73 (m, 1H), 4.33 (s, 2H), 3.68-3.38 (m, 8H).

Example 14

Compound (14): Preparation of 4-(3-(4-(1H-imidazo[4,5-b]pyridin-5-yl)piperazine-1-carbonyl)-4-methoxybenzyl)phthalazin-1(2H)-one The reaction scheme was specifically as follows.

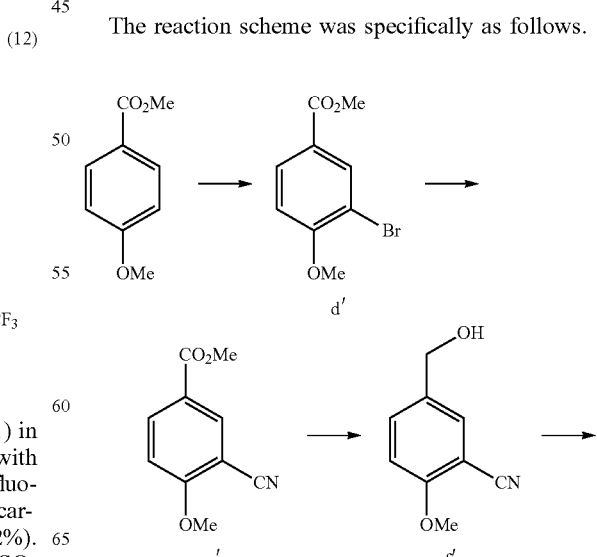

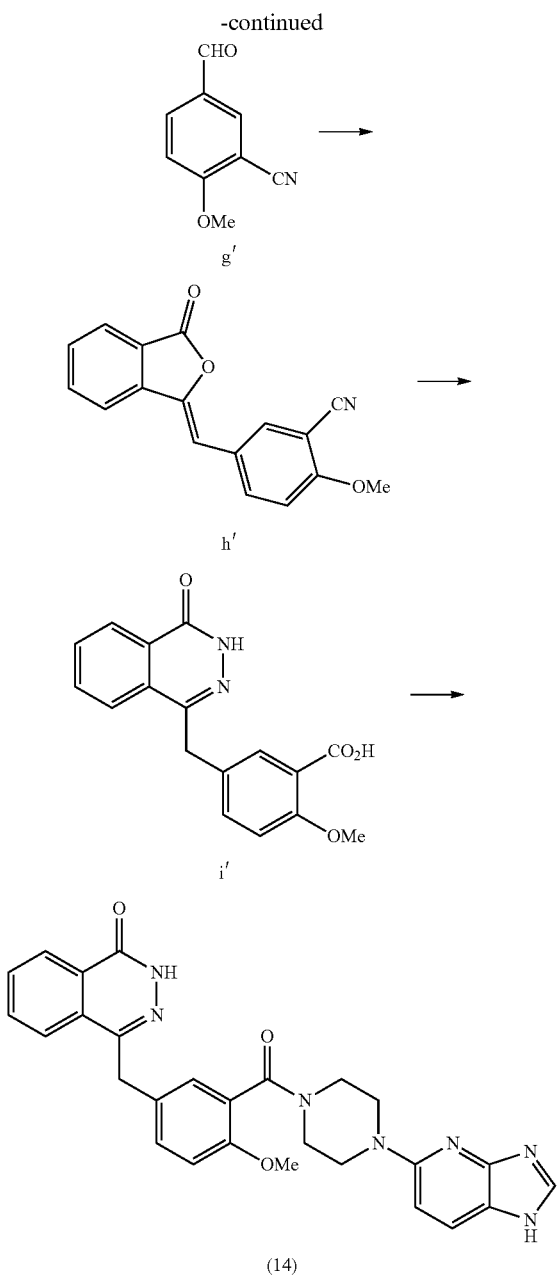

Step 1: Preparation of methyl 3-bromo-4-methoxybenzoate

To a solution of methyl 4-methoxybenzoate (1.5 g, 9 mol) dissolved in water (10 mL), potassium bromate (251 mg, 1.5 mmol) and liquid bromine (722 mg, 4.5 mmol) were slowly added at room temperature. The reaction system was stirred for 2.5 hrs while the temperature was maintained below 30° C. The reaction system was added with methyl t-butyl ether (25 mL), and extracted. Then, the organic phase was washed with saturated saline, dried and concentrated. The resulting residue was separated by flash column chromatography (petroleum ether:ethyl acetate=10:1) to obtain Compound d': methyl 3-bromo-4-methoxybenzoate as a white solid (2.1 g, yield 95%).

Step 2: Preparation of methyl 3-cyano-4-methoxybenzoate

To a solution of Compound d' (1.1 g, 4.4 mol) dissolved in dimethyl formamide (10 mL), cuprous cyanide (1.2 g, 13.22 mmol) was added, heated to 140° C., and stirred for 6 hrs. The reaction system was cooled, added with ethyl acetate (25 mL), and extracted. Then, the organic phase was washed with saturated saline, dried and concentrated. The resulting residue was separated by flash column chromatography (petroleum ether:ethyl acetate=10:1), to obtain Compound e': methyl 3-cyano-4-methoxybenzoate as a white solid (662 mg, yield 79%).

Step 3: Preparation of 5-(hydroxymethyl)-2-methoxybenzonitrile

To a solution of Compound e' (1 g, 5.2 mol) dissolved in tetrahydrofuran (25 mL), lithium borohydride (0.45 g, 20.7 mmol) was added, and stirred overnight at room temperature. The reaction system was dried and concentrated. The resulting residue was separated by flash column chromatography (petroleum ether:ethyl acetate=2:1), to obtain Compound f: 5-(hydroxymethyl)-2-methoxybenzonitrile as a white solid (845 mg, yield 100%).

Step 4: Preparation of 5-formyl-2-methoxybenzonitrile

To a solution of Compound f (845 mg, 5.2 mol) dissolved in dichloromethane (50 mL), (1,1,1-triacetyloxy)-1,1-dihydro-1,2-benziodoxol-3(1H)-one (2.6 g, 6.2 mmol) was added and stirred for 2 hrs at room temperature. The reaction system was dried and concentrated. The resulting residue was separated by flash column chromatography (petroleum ether:ethyl acetate=3:1) to obtain Compound g': 5-formyl-2-methoxybenzonitrile as a white solid (845 mg, yield 100%).

Step 5: Preparation of 2-methoxy-5-((3-oxoisobenzofuran-1(3H)-ylidene)methyl)phenol Analogous to the process for preparing Compound e in Step 5 in Example 1, Compound g' was reacted with 3-oxo-1,3-dihydroisobenzofuran-1-yldimethyl phosphite to produce Compound h': 2-methoxyoxoisobenzofuran-1(3H)-ylidene)methyl)benzonitrile (795 mg, yield 67%).

Step 6: Preparation of 2-methoxy-5-((4-oxo-3,4-dihydrophthalazin-1-yl)methyl)benzoic acid Analogous to the process for preparing Compound f in Step 6 in Example 1, Compound h' was hydrolyzed to produce Compound i': 2-methoxy-5-((4-oxo-3,4-dihydrophthalazin-1-yl)methyl)benzoic acid (318 mg, yield 63%). MS (ESI) m/z: 311 [M+1]+.

Step 7: Preparation of 4-(3-(4-(1H-imidazo[4,5-b]pyridin-5-yl)piperazine-1-carbonyl)-4-methoxybenzyl)phthalazin-1(2H)-one Analogous to the process for preparing Compound (1) in Step 7 in Example 1, Compound i' was condensed with Compound 1 to produce Compound (14): 4-(3-(4-(1H-imidazo[4,5-b]pyridin-5-yl)piperazine-1-carbonyl)-4-methoxybenzyl)phthalazin-1(2H)-one (77 mg, yield 49%). MS (ESI) m/z: 496 [M+1]+. 1HNMR (300 MHz, DMSO-d6): δ 12.55

(br, 1H), 8.23 (d, 1H, J=7.6 Hz), 8.19 (s, 1H), 7.95 (d, 1H, J=8.4 Hz), 7.88-7.80 (m, 3H), 7.39-7.31 (m, 1H), 7.16-7.15 (m, 1H), 7.01 (d, 1H, J=8.4 Hz), 6.80 (d, 1H, J=9.2 Hz), 4.24 (s, 2H), 3.73 (s, 3H), 3.70-3.69 (m, 2H), 3.55-3.54 (m, 2H), 3.37-3.36 (m, 2H), 3.18-3.16 (m, 2H).

Example 15

Compound (15): Preparation of 4-(3-(4-(1H-imidazo[4,5-b]pyridin-5-yl)piperazine-1-carbonyl)-4-trifluoromethylbenzyl)phthalazin-1(2H)-one The reaction scheme was specifically as follows.

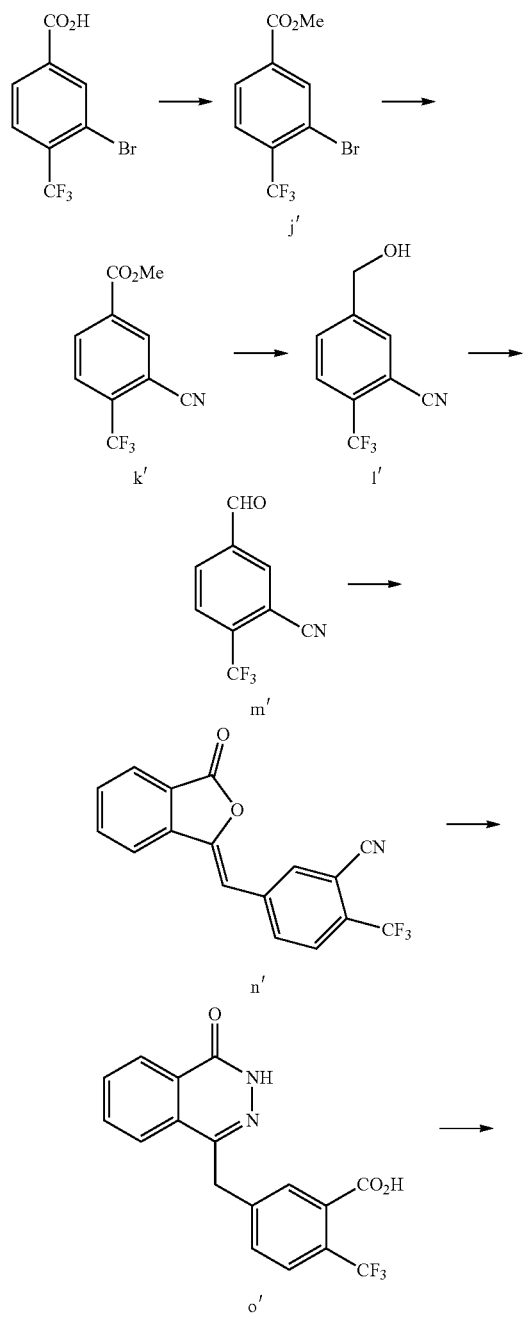

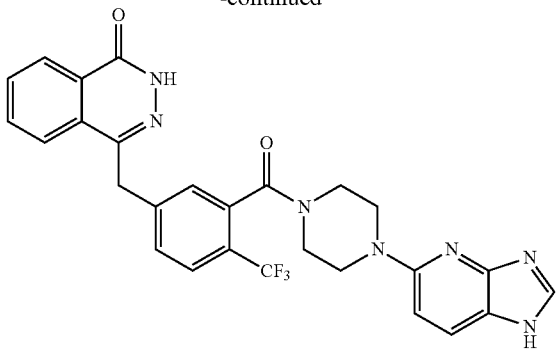

(15)

Step 1: Preparation of methyl 3-bromo-4-trifluoromethylbenzoate

To a solution of 3-bromo-4-trifluoromethylbenzoic acid (4.1 g, 15.4 mol) dissolved in methanol (30 mL), concentrated sulfuric acid (1 mL) was slowly added at room temperature. The reaction system was heated to 60° C. and stirred for 6 hrs. After cooling to room temperature, the reaction system was extracted with ethyl acetate (25 mL). The organic phase was washed with saturated saline, dried and concentrated. The resulting residue was separated by flash column chromatography (petroleum ether:ethyl acetate=10:1) to obtain Compound j': methyl 3-bromo-4-trifluoromethylbenzoate as a white solid (4.2 g, yield 96%).

Step 2: Preparation of methyl 3-cyano-4-trifluoromethylbenzoate

Analogous to the process for preparing Compound e' in Step 2 in Example 14, Compound j' was cyanidated to produce Compound k': methyl 3-cyano-4-trifluoromethylbenzoate (1.6 g, yield 64%). MS (ESI) m/z: 230 [M+1]$^+$.

Step 3: Preparation of 5-(hydroxymethyl)-2-trifluoromethylbenzonitrile

Analogous to the process for preparing Compound f' in Step 3 in Example 14, Compound k' was reduced to produce Compound l': 5-(hydroxymethyl)-2-trifluoromethylbenzonitrile (1.2 g, yield 87%). MS (ESI) m/z: 202 [M+1]$^+$.

Step 4: Preparation of 5-formyl-2-trifluoromethylbenzonitrile

Analogous to the process for preparing Compound g' in Step 4 in Example 14, Compound l' was reduced to produce Compound m': 5-formyl-2-trifluoromethylbenzonitrile (1.3 g, yield 96%). MS (ESI) m/z: 200 [M+1]$^+$.

Step 5: Preparation of 2-trifluoromethyl-5-((3-oxoisobenzofuran-1(3H)-ylidene)methyl)benzonitrile Analogous to the process for preparing Compound e in Step 5 in Example 1, Compound m' was reacted with 3-oxo-1,3-dihydroisobenzofuran-1-yldimethyl phosphite to produce Compound n': 2-trifluoromethyl-5-((3-oxoisobenzofuran-1(3H)-ylidene)methyl)benzonitrile (721 mg, yield 69%).

Step 6: Preparation of 2-trifluoromethyl-5-((4-oxo-3,4-dihydrophthalazin-1-yl)methyl)benzoic acid Analogous to the process for preparing Compound f in Step 6 in Example 1, Compound n' was hydrolyzed to produce Compound o': 2-trifluoromethyl-5-((4-oxo-3,4-dihydrophthalazin-1-yl)methyl)benzoic acid (678 mg, yield 86%). MS (ESI) m/z: 349 [M+1]+.

Step 7: Preparation of 4-(3-(4-(1H-imidazo[4,5-b]pyridin-5-yl)piperazine-1-carbonyl)-4-trifluoromethylbenzyl)phthalazin-1(2H)-one Analogous to the process for preparing Compound (1) in Step 7 in Example 1, Compound o' was condensed with Compound 1 to produce Compound (15): 4-(3-(4-(1H-imidazo[4,5-b]pyridin-5-yl)piperazine-1-carbonyl)-4-trifluoromethylbenzyl)phthalazin-1(2H)-one (65 mg, yield 53%). MS (ESI) m/z: 534 [M+1]+.

¹HNMR (300 MHz, DMSO-d6):

δ 12.57 (s, 1H), 8.24 (d, 1H, J=0.8 Hz), 8.23 (s, 1H), 7.96-7.80 (m, 4H), 7.73 (d, 1H, J=8.0 Hz), 7.54 (d, 1H, J=8.0 Hz), 7.50 (s, 1H), 6.77 (d, 1H, J=8.4 Hz), 4.42 (s, 2H), 3.82-3.77 (m, 1H), 3.68-3.62 (m, 1H), 3.59-3.52 (m, 2H), 3.36-3.29 (m, 2H), 3.19-3.10 (m, 2H).

Example 16

Compound (16): Preparation of 4-(3-(4-(1H-[1,2,3]triazolo[4,5-b]pyridin-5-yl)piperazine-1-carbonyl)-4-trifluoromethylbenzyl)phthalazin-1(2H)-one The reaction scheme was specifically as follows.

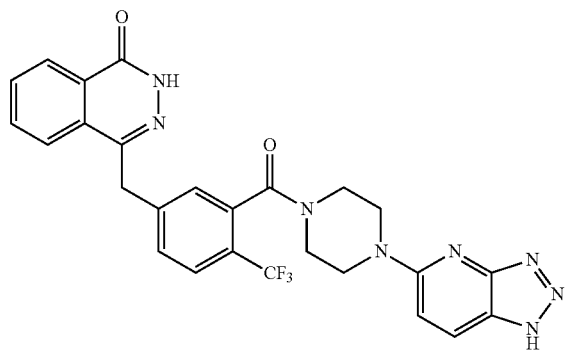

(16)

Analogous to the process for preparing Compound (1) in Step 7 in Example 1, Compound o' was condensed with Compound d to produce Compound (16): 4-(3-(4-(1H-[1,2,3]triazolo[4,5-b]pyridin-5-yl)piperazine-1-carbonyl)-4-trifluoromethylbenzyl)phthalazin-1(2H)-one (70 mg, yield 57%). MS (ESI) m/z: 535 [M+1]+.

¹HNMR (300 MHz, DMSO-d6): δ 12.57 (s, 1H), 8.24 (d, 1H, J=7.2 Hz), 8.17 (d, 1H, J=8.8 Hz), 7.95-7.81 (m, 3H), 7.74 (d, 1H, J=8.0 Hz), 7.55 (d, 1H, J=8.0 Hz), 7.51 (s, 1H), 6.98 (d, 1H, J=9.6 Hz), 4.42 (s, 2H), 3.80-3.62 (m, 4H), 3.50-3.46 (m, 2H), 3.36-3.30 (m, 2H).

Example 17

Compound (17): Preparation of 4-(3-(4-(2-oxo-2,3-dihydro-1H-imidazo[4,5-]pyridin-5-yl)piperazine-1-carbonyl)-4-trifluoromethylbenzyl)phthalazin-1(2H)-one The reaction scheme was specifically as follows.

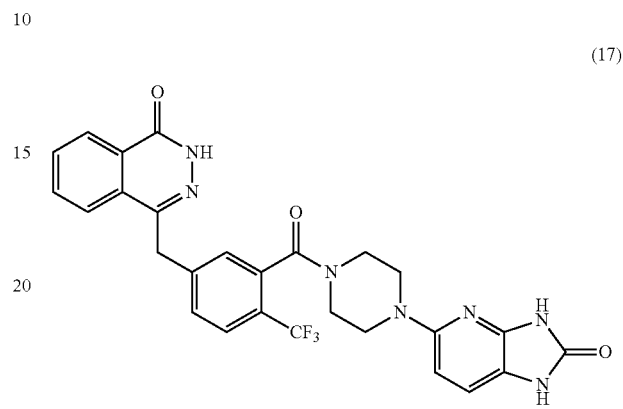

(17)

Analogous to the process for preparing Compound (1) in Step 7 in Example 1, Compound o' was condensed with Compound n to produce Compound (17): 4-(3-(4-(2-oxo-2,3-dihydro-1H-imidazo[4,5-b]pyridin-5-yl)piperazine-1-carbonyl)-4-trifluoromethylbenzyl)phthalazin-1(2H)-one (67 mg, yield 53%). MS (ESI) m/z: 550 [M+1]+.

¹HNMR (300 MHz, DMSO-d6):

δ 12.57 (s, 1H), 10.95 (s, 1H), 10.37 (s, 1H), 8.23 (d, 1H, J=7.2 Hz), 7.94-7.80 (m, 3H), 7.73 (d, 1H, J=8.0 Hz), 7.54 (d, 1H, J=8.0 Hz), 7.47 (s, 1H), 7.09 (d, 1H, J=8.0 Hz), 6.33 (d, 1H, J=8.0 Hz), 4.42 (s, 2H), 3.70-3.64 (m, 1H), 3.64-3.59 (m, 1H), 3.42-3.25 (m, 2H), 3.14-3.08 (m, 4H).

Example 18

Compound (18): Preparation of 4-(3-(4-(3H-imidazo[4,5-c]pyridin-6-yl)piperazine-1-carbonyl)-4-methoxybenzyl)phthalazin-1(2H)-one The reaction scheme was specifically as follows.

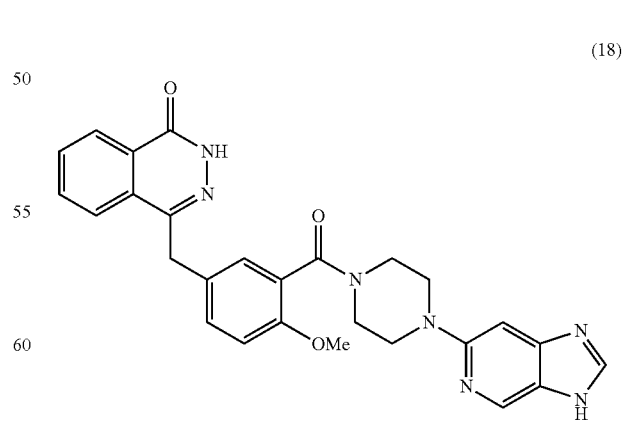

(18)

Analogous to the process for preparing Compound (1) in Step 7 in Example 1, Compound i' was condensed with Compound r to produce Compound (18): 4-(3-(4-(3H-imidazo[4,5-c]pyridin-6-yl)piperazine-1-carbonyl)-4-methoxybenzyl)phthalazin-1(2H)-one (54 mg, yield 34%). MS (ESI) m/z: 496 [M+1]+. ¹HNMR (300 MHz, DMSO-d6): δ 12.55 (s, 1H), 8.56 (s, 1H), 8.23 (s, 1H), 8.22 (s, 1H), 7.93 (d, 1H, J=8.0 Hz), 7.87-7.77 (m, 3H), 7.31 (d, 1H, J=8.0 Hz), 7.15 (s, 1H), 7.0 (d, 1H, J=8.0 Hz), 6.82 (s, 1H), 4.23 (s, 2H), 3.71 (br, 5H), 3.47-3.46 (m, 2H), 3.32-3.18 (m, 4H).

Example 19

Compound (19): Preparation of 4-(3-(4-(3H-imidazo[4,5-c]pyridin-6-yl)piperazine-1-carbonyl)-4-trifluoromethylbenzyl)phthalazin-1(2H)-one The reaction scheme was specifically as follows.

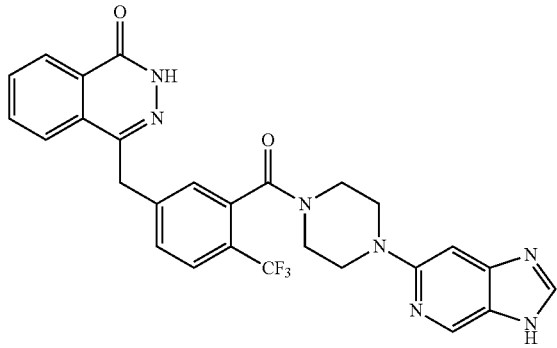

(19)

Analogous to the process for preparing Compound (1) in Step 7 in Example 1, Compound o' was condensed with Compound r to produce Compound (19): 4-(3-(4-(3H-imidazo[4,5-c]pyridin-6-yl)piperazine-1-carbonyl)-4-methoxybenzyl)phthalazin-1(2H)-one (46 mg, yield 46%). MS (ESI) m/z: 534 [M+1]+. ¹HNMR (300 MHz, DMSO-d6): δ 12.57 (s, 1H), 8.55 (s, 1H), 8.24 (d, 1H, J=8.0 Hz), 8.17 (s, 1H), 7.95-7.72 (m, 5H), 7.55 (d, 1H, J=8.0 Hz), 7.48 (s, 1H), 6.80 (s, 1H), 4.43 (s, 2H), 3.81-3.79 (m, 1H), 3.78-3.77 (m, 1H), 3.68-3.64 (m, 2H), 3.49-3.46 (m, 2H), 3.17-3.12 (m, 2H).

Example 20

Compound (20): Preparation of 4-(3-(4-(3H-imidazo[4,5-b]pyridin-6-yl)piperazine-1-carbonyl)-4-trifluoromethylbenzyl)phthalazin-1(2H)-one The reaction scheme was specifically as follows

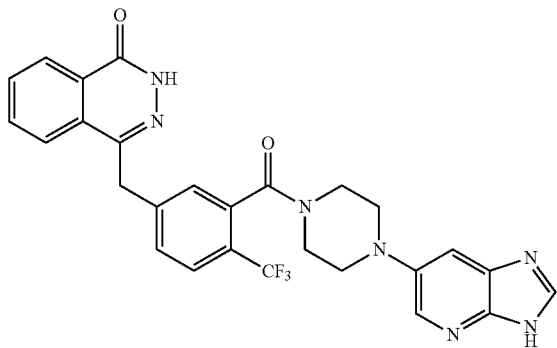

(20)

Analogous to the process for preparing Compound (1) in Step 7 in Example 1, Compound o' was condensed with Compound v to produce Compound (20): 4-(3-(4-(3H-imidazo[4,5-b]pyridin-6-yl)piperazine-1-carbonyl)-4-trifluoromethylbenzyl)phthalazin-1(2H)-one (37 mg, yield 41%). MS (ESI) m/z: 534 [M+1]+. ¹HNMR (300 MHz, DMSO-d6): δ 12.57 (s, 1H), 8.47 (s, 1H), 8.24 (s, 1H), 8.22 (s, 1H), 7.95-7.73 (m, 5H), 7.55 (d, 1H, J=8.0 Hz), 7.50 (s, 1H), 7.49 (s, 1H), 4.43 (s, 2H), 3.85-3.82 (m, 1H), 3.73-3.70 (m, 1H), 3.20-3.19 (m, 4H), 2.98 (m, 2H).

Example 21

Compound (21): Preparation of 4-(3-(4-(3H-imidazo[4,5-b]pyridin-6-yl)piperazine-1-carbonyl)-4-methoxybenzyl)phthalazin-1(2H)-one The reaction scheme was specifically as follows.

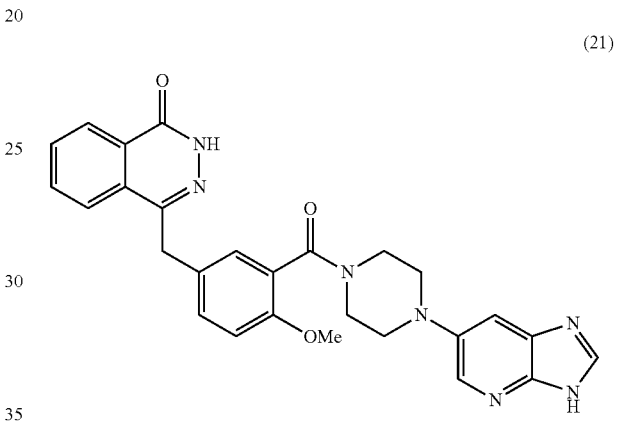

(21)

Analogous to the process for preparing Compound (1) in Step 7 in Example 1, Compound i' was condensed with Compound v to produce Compound (21): 4-(3-(4-(3H-imidazo[4,5-b]pyridin-6-yl)piperazine-1-carbonyl)-4-methoxybenzyl)phthalazin-1(2H)-one (66 mg, yield 42%). MS (ESI) m/z: 496 [M+1]+. ¹HNMR (300 MHz, DMSO-d6): δ 12.55 (s, 1H), 8.37 (s, 1H), 8.23 (s, 1H), 8.21 (s, 1H), 7.94-7.76 (m, 3H), 7.49 (s, 1H), 7.31 (d, 1H, J=8.0 Hz), 7.15-7.12 (m, 1H), 7.00 (d, 1H, J=8.0 Hz), 6.93 (s, 1H), 4.23 (s, 2H), 3.77 (s, 3H), 3.76 (br, 2H), 3.23-3.13 (m, 4H), 3.05-2.97 (m, 2H).

Biological Evaluation

Example 1: PARP Enzyme Activity Assay

Experimental Principle:
Poly(ADP-ribosyl)ation of nuclear proteins is a post-translational modification occurred in response to DNA damage. PARP is the abbreviation of poly(ADP-ribose) polymerase, which catalyzes the attachment of poly(ADP-ribose) to an adjacent nuclear protein in the presence of NAD, thus eliciting a mechanism of DNA repair through base excision repair pathway. The level of biotin-labeled ADP-ribose binding to histone can be detected by using the HT Universal Chemiluminescent PARP Assay Kit commercially available from Trevigen Corp.

Reagents and Materials
1. HT Universal Chemiluminescent PARP Assay Kit with Histone-coated Strip Wells, commercially available from Trevigen (US), Catalog #: 4676-096-K.
2. Plate reader: EnVision Multilabel Plate Reader available from Perkin Elmer (US).

Solutions and Buffers

1. Washing buffer: 0.1% Triton X-100 in PBS.

2. 20×PARP buffer—It was 1:20 diluted in deionized water to obtain a 1× buffer, which was used for diluting the recombinant PARP enzyme, PARP Cocktails, and test compounds.

3. 10×PARP Cocktail was formulated into a 1×PARP Cocktail by mixing 10×PARP Cocktail 2.5 µl/well, 10× activated DNA 2.5 µl/well, and 1×PARP buffer 20 µl/well.

4. The PARP enzyme was carefully diluted with the 1×PARP buffer just before use, the diluted enzyme solution should be used as quickly as possible and the remaining solution should be discarded.

5. Strep-HRP was 1:500 diluted with the 1× Strep diluent just before use to obtain a 1× solution.

6. The chemiluminescent substrate was prepared just before use, by uniformly mixing equal volume of Peroxy-Glow A and B to obtain a substrate for horseradish peroxidase.

Experimental Method

Formulation of Compound Solutions 1. 10 mM stock solution of each test compound was diluted to 10 µM, and 1 µM in DMSO.

2. Just before experiment, the solution at various concentration gradients of each compound dissolved in DMSO was 1:20 diluted in the 1×PARP buffer, to obtain a 5× compound solution for test. The positive and negative control wells contained the 1×PARP buffer (containing 5% DMSO). AZD2281 (Olaparib, AstraZeneca PLC) was used as the control compound.

Experimental Procedures 1. 50 µl of 1×PARP buffer per well was added to infiltrate the histone, and the plate was incubated for 30 min at room temperature. Then the 1×PARP buffer in each well was aspirated, and the remaining liquid was tapped dry on paper towels.

2. The diluted 5× solutions of Compounds (1) to (21) and the control compound AZD2281 were added to respective wells (10 µl per well). The positive and negative control wells contained the 1×PARP buffer (containing 5% DMSO).

3. The PARP enzyme was diluted in the 1×PARP buffer to give a concentration of 0.5 Unit per 15 µl, and then 15 µl of the enzyme solution was added to each well except that the negative control well was added exclusively with the 1×PARP buffer. The plate was incubated for 10 min at room temperature.

4. 25 µl of the 1×PARP Cocktail was sequentially added to each well.

5. The plate was incubated for 60 min at 27° C.

6. After incubation, the reaction solution was aspirated from the wells, and the remaining liquid was tapped dry on paper towels. Then, the plate was washed 4 times with 0.1% Triton X-100 in PBS (200 µl per well per wash), and the remaining liquid was tapped dry on paper towels.

7. Subsequently, the diluted 1× Strep-HRP solution was added to each well, and then the plate was incubated for 60 min at 27° C.

8. After incubation, the reaction solution was aspirated from the wells, and the remaining liquid was tapped dry on paper towels. Then, the plate was washed 4 times with 0.1% Triton X-100 in PBS (200 µl per well per wash), and the remaining liquid was tapped dry on paper towels.

9. After washing, equal volume of the PeroxyGlow A and B solutions were uniformly mixed, 100 µl of the solution was added to each well, and the chemiluminescent signals were recorded on a plate reader immediately.

Data Processing

The readout of each well is converted into the percent inhibition. The percent inhibition of the compounds may be calculated by an equation below:

$$\text{Inhibition}(\%) = \frac{\text{Readout of positive control well} - X}{\text{Readout of positive control well} - \text{Readout of negative control well}} \times 100\%$$

Note: the readout of the positive control well is designated as 100% enzyme activity; the readout of the negative control well is designated as 0% enzyme activity; and the activity X refers to the readout from respective concentration of each sample.

TABLE 1

Inhibition of the compounds on PARP-1 enzyme

| No. of Example Compound | IC$_{50}$ (PARP)/nM |
|---|---|
| (1) | 2 |
| (2) | 9 |
| (3) | 6 |
| (4) | 1 |
| (5) | 1 |
| (6) | 3 |
| (7) | 8 |
| (8) | 11 |
| (9) | 2 |
| (10) | 5 |
| (11) | 17 |
| (12) | 10 |
| (13) | 1 |
| (14) | 4 |
| (15) | 2 |
| (16) | 7 |
| (17) | 6 |
| (18) | 13 |
| (19) | 8 |
| (20) | 2 |
| (21) | 15 |
| Control Compound AZD2281 | 8 |

Conclusion: Preferred compounds of the present invention have a markable inhibitory activity on the proliferation of PARP-1 enzyme.

Example 2. Cell Proliferation Inhibition Assay

The proliferation inhibitory activity of the compound of the present invention on the breast cancer cell line MDA-MB-436 of triple negative phenotype was tested in vitro.

Reagents and Materials

1. Tumor cell line MDA-MB-436 supplied from HD Biosciences (Shanghai) Co., Ltd., and passed the Mycoplasma detection.

2. L15 culture medium, Invitrogen, Catalog #: 11415-064.

3. Fetal bovine serum, Hyclone, Catalog #: CH30160.03.

4. Penicillin-streptomycin liquid, Invitrogen, Catalog #: 15140-122.

5. DMSO, Sigma, Catalog #D4540.

6. 96-well plate, Corning, Catalog #: 3610.

7. CellTiter-Glo Luminescent Cell Viability Assay, Promega, Catalog #: G7571.

8. Plate reader: EnVision Multilabel PlateReader available from Perkin Elmer.

Cell Culture Medium

1. L15 medium. L15 complete cell culture medium: L15 medium containing 10% fetal bovine serum, 100 U penicillin and 100 µg/ml streptomycin Experimental Method
Formulation of Compound Solutions 1. Each test compound was formulated into a 60 mM stock solution in DMSO, packaged, and stored in a freezer at −80°. The stock solution of each test compound was serially diluted in DMSO to give solutions at various concentration gradients, including 6 mM, 2 mM, 0.6 mM, 0.2 mM, 60 µM, and 20 µM.

2. Just before experiment, the formulated solution at various concentration gradients of each test compound was aseptically 100-fold diluted in the complete cell culture medium. In this case, the concentration gradients of the test compound included 60 µM, 20 µM, 6 µM, 2 µM, 0.6 µM, and 0.2 µM. These were 2× compound solutions, and could be used to treat the cells.

3. The stock solution of Compounds (1) to (21) and the control compound AZD2281 was serially diluted in DMSO to give solutions at various concentration gradients, including 20 µM, 2 µM, 0.2 µM, 0.02 µM, 0.002 µM, and 0.0002 µM. Before experiment, the formulated solution at various concentration gradients of each test compound was aseptically 100-fold diluted in the complete cell culture medium. The concentration gradients of the positive compound included 200 nM, 20 nM, 2 nM, 0.2 nM, 0.02 nM, and 0.002 nM. These were 2× compound solutions, and could be used to treat the cells.

Experimental Procedures

1. One day before treatment with the compounds, the cells were inoculated into a 96-well plate at a density of 8000 cells/50 µl/well.

2. On the following day, the formulated 2× compound solutions were added, in accordance with a compound arrangement pattern, to the plate in an amount of 50 µl/well.

3. The plate was gently agitaged, and incubated for 120 hrs in an incubator at 37° C.

4. After incubation, the formulated reagent was added to the plate following instruction of the CellTiter Glo reagent, fully mixed, and incubated for 10 min at room temperature in the dark.

5. The plate was analyzed on a plate reader, the chemiluminescence was read, and the data was recorded.

Data Processing

The reading of each well needs to be converted into cell viability. The cell viability can be calculated using the following formula:

$$\text{Cell viability (\%)} = \frac{\text{Reading of sample well}}{\text{Reading of solvent control well}} \times 100\%$$

The processed data was subjected to non-linear regression analysis by using the GraphPad Prism5 analysis software, to obtain a dose-response curve; and the median effective dose ($ED_{50}$) of test compounds for the MDA-MB-436 cells was calculated.

TABLE 2

| Proliferation inhibition of compounds on MDA-MB-436 cells | |
|---|---|
| Example Compound No. | $ED_{50}$ (MDA-MB-436)/µM |
| (1) | >25 |
| (2) | >25 |
| (3) | >25 |
| (4) | 0.7 |
| (5) | >25 |
| (6) | 18 |
| (7) | >25 |
| (8) | 1.4 |
| (9) | >25 |
| (10) | >25 |
| (11) | >25 |
| (12) | >25 |
| (13) | 0.7 |
| (14) | 6.8 |
| (15) | 23 |
| (16) | >25 |
| (17) | >25 |
| (18) | >25 |
| (19) | >25 |
| (20) | >25 |
| (21) | >25 |
| Control compound AZD2281 | >25 |

Conclusion: Some preferred compounds of the present invention have a significant inhibitory activity against the proliferation of MDA-MB-436 cells.

Example 3. Test of Tumor Inhibition Effect of Compounds of the Present Invention in Mice The following experiments were conducted to evaluate and compare the effects of the present compound alone in mice tumor models transplanted with human breast cancer cell line MDA-MB-436, human breast cancer cell line MX-1 or human pancreatic cancer cell line CAPAN-1 in vivo.

Test Compound: Example Compound (4)

Test Animal

BALB/cA-nude mice, 6-7 weeks, female, available from Shanghai SLAC Laboratory Animal Co., Ltd. Certificate number: SCXK (Shanghai) 2012-0002. Breeding environment: SPF grade.

Experimental Procedures

The Nude mice were subcutaneously inoculated with human breast cancer MDA-MB-436 cells, human breast cancer MX-1 cells or human pancreatic cancer CAPAN-1 cells. After the tumor grew to 100-200 mm$^3$, the animals were grouped at random (D0). The Dosage and dosing regimen were shown in Table 1. The tumor volume was measured twice or thrice a week, the body weight of the mice was weighed, and the data was recorded. The tumor volume (V) is calculated by using a formula below:

$$V = \tfrac{1}{2} \times a \times b^2$$

in which a, and b denote the length and width.

$$T/C(\%) = (T-T_0)/(C-C_0) \times 100$$

in which T are C are the tumor volumes at the end of the experiment; and $T_0$ and $C_0$ are the tumor volumes at the beginning of the experiment.

TABLE 3

Dosage, dosing regimen and tumor inhibition effect of compounds in nude mice tumor model transplanted with Human breast cancer MDA-MB-436 cells

| Compound | Route of administration | Dosage | Frequency of administration | Days of administration | Tumor inhibition |
|---|---|---|---|---|---|
| Compound (4) | Oral | 30 mg/kg | Once a day | Consecutive 14 days | 191% |
| AZD2281 | Oral | 30 mg/kg | Once a day | Consecutive 14 days | 83% |

Conclusion: Some preferred compounds of the present invention have obvious anti-cancer activity in nude mice tumor model transplanted with Human breast cancer MDA-MB-436 cells, when administered alone.

TABLE 4

Dosage, dosing regimen and tumor inhibition effect of compounds in nude mice tumor model transplanted with Human breast cancer MX-1 cells

| Compound | Route of administration | Dosage | Frequency of administration | Days of administration | Tumor inhibition |
|---|---|---|---|---|---|
| Compound (4) | Oral | 50 mg/kg | Once a day | Consecutive 21 days | 193% |
| AZD2281 | Oral | 50 mg/kg | Once a day | Consecutive 21 days | 13% |

Conclusion: Some preferred compounds of the present invention have obvious anti-cancer activity in nude mice tumor model transplanted with Human breast cancer MX-1 cells, when administered alone.

TABLE 5

Dosage, dosing regimen and tumor inhibition effect of compounds in nude mice tumor model transplanted with Human pancreatic cancer CAPAN-1 cells

| Compound | Route of administration | Dosage | Frequency of administration | Days of administration | Tumor inhibition |
|---|---|---|---|---|---|
| Compound (4) | Oral | 50 mg/kg | Once a day | Consecutive 21 days | 128% |
| AZD2281 | Oral | 50 mg/kg | Once a day | Consecutive 21 days | 57% |

Conclusion: Some preferred compounds of the present invention have obvious anti-cancer activity in nude mice tumor model transplanted with Human pancreatic cancer CAPAN-1 cells, when administered alone.

What is claimed is:

1. A compound of Formula I

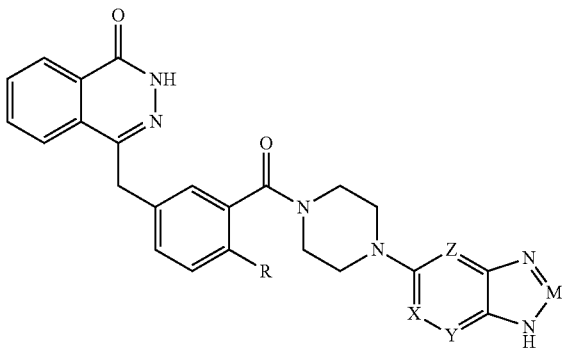

or a tautomer thereof,
or a pharmaceutically acceptable salt thereof: wherein in Formula I, R is hydrogen, halo, $C_1$-$C_6$ alkoxy or $C_1$-$C_6$ haloalkyl; one of X, Y, and Z is nitrogen, and the others are CH; or one of X, Y, and Z is CH, and the others are nitrogen; and M is nitrogen or $CR_1$, in which $R_1$ is hydrogen, oxo, alkyl, alkoxy or haloalkyl.

2. The compound of Formula I according to claim 1, wherein R is hydrogen, halo, $C_1$-$C_3$ alkoxy or C $C_1$-$C_3$ haloalkyl.

3. The compound of claim 1, wherein R is hydrogen, fluoro, methoxy or trifluoromethyl.

4. The compound of claim 1, wherein X is nitrogen, and Y and Z are CH; or Z is nitrogen, and X and Y are CH; or Y is nitrogen, and X and Z are CH; or X and Z are nitrogen, and Y is CH.

5. The compound of claim 1, wherein $R_1$ is hydrogen, oxo, $C_1$-$C_6$ alkyl or $C_1$-$C_6$ haloalkyl.

6. The compound of claim 1, wherein $R_1$ is hydrogen, oxo, $C_1$-$C_3$ alkyl or $C_1$-$C_3$ haloalkyl.

7. The compound of claim 1, wherein $R_1$ is hydrogen, oxo, methyl or trifluoromethyl.

8. The compound of claim 1, which is selected from the group consisting of Compounds 1 to 21 or a pharmaceutically acceptable salt thereof:

1
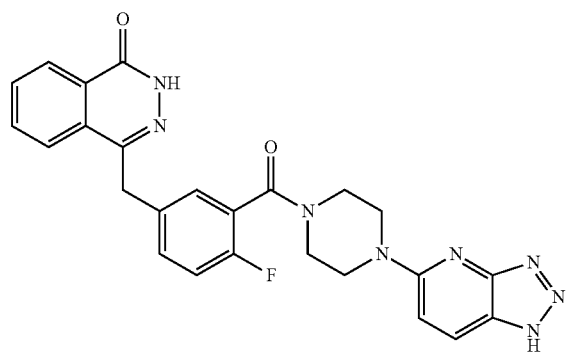
2
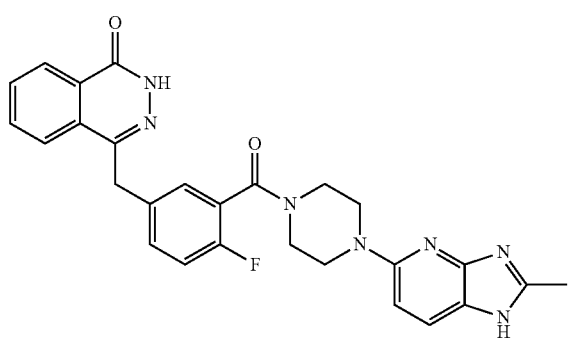
3
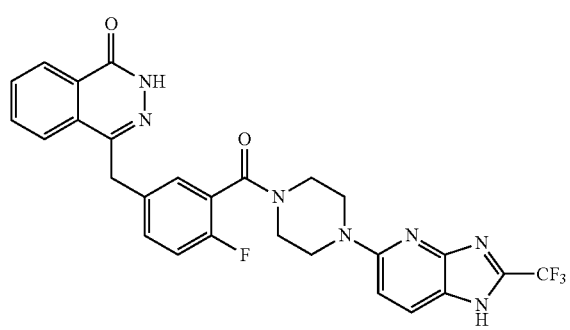
4
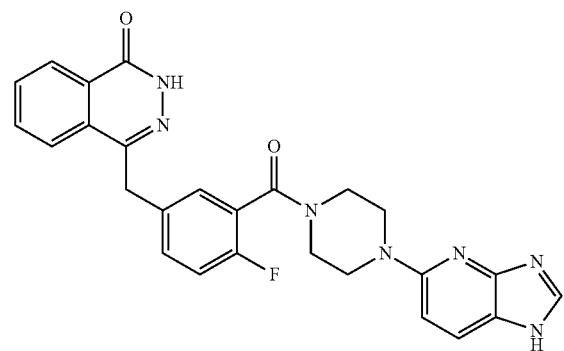
5
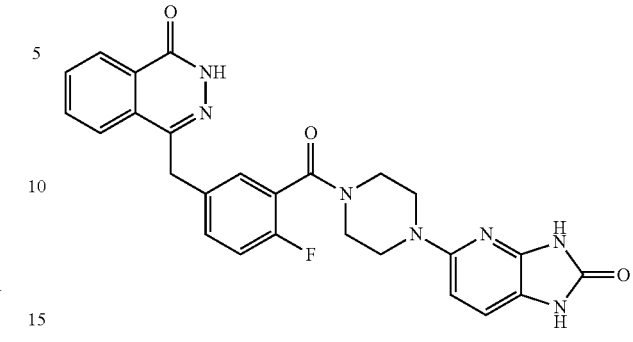

9
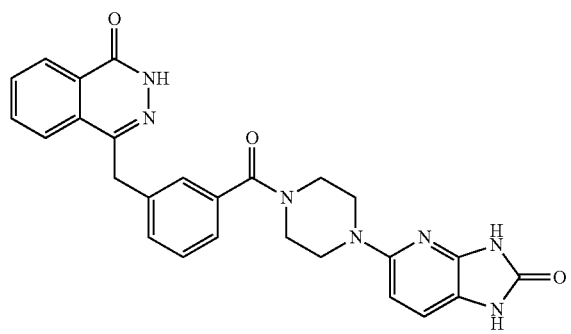
10
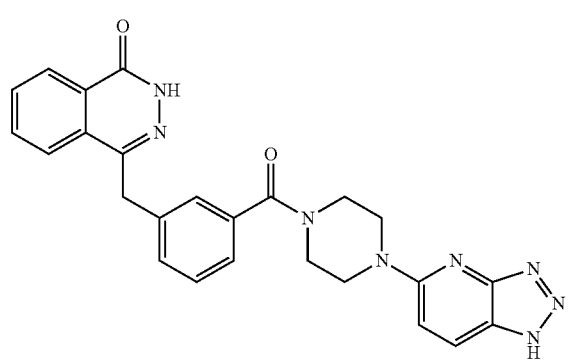
11
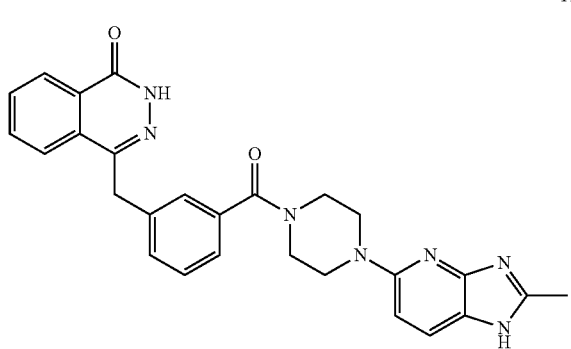
12
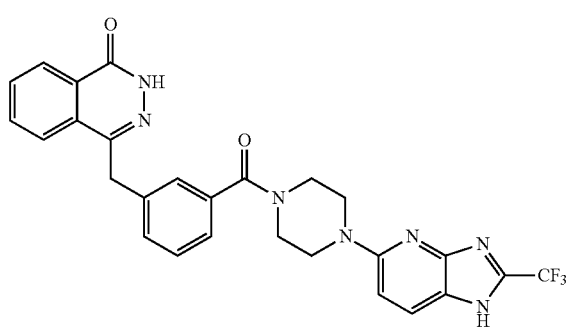
13
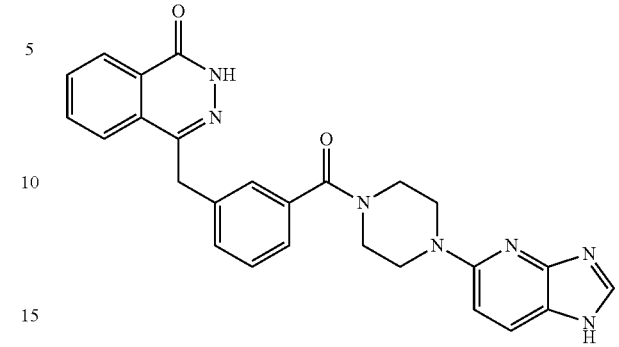
14
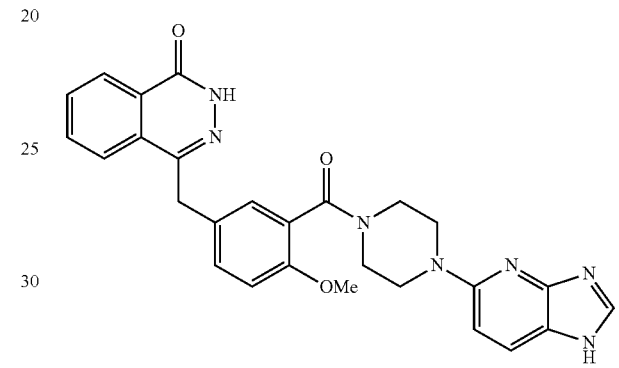
15
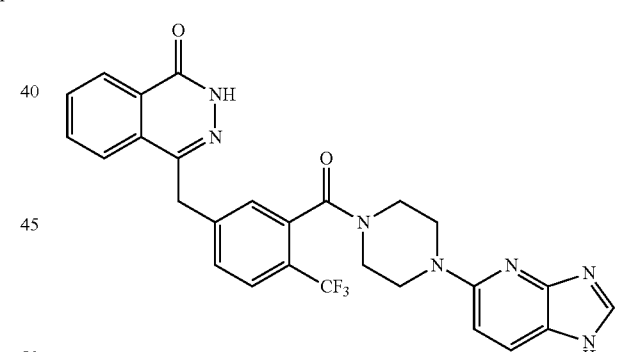
16
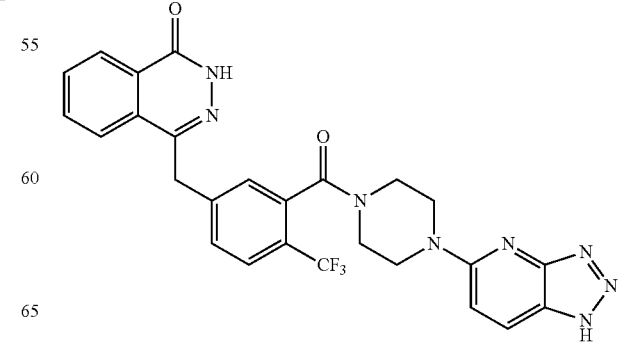

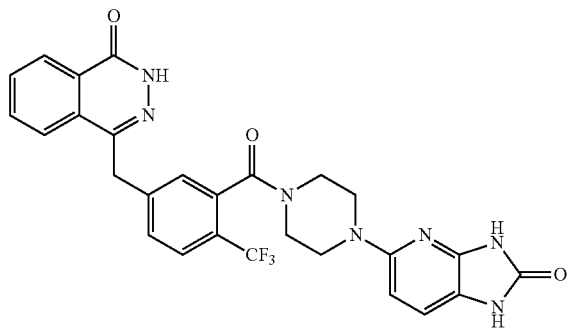
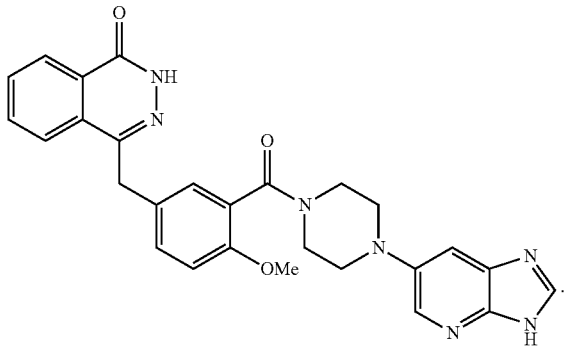
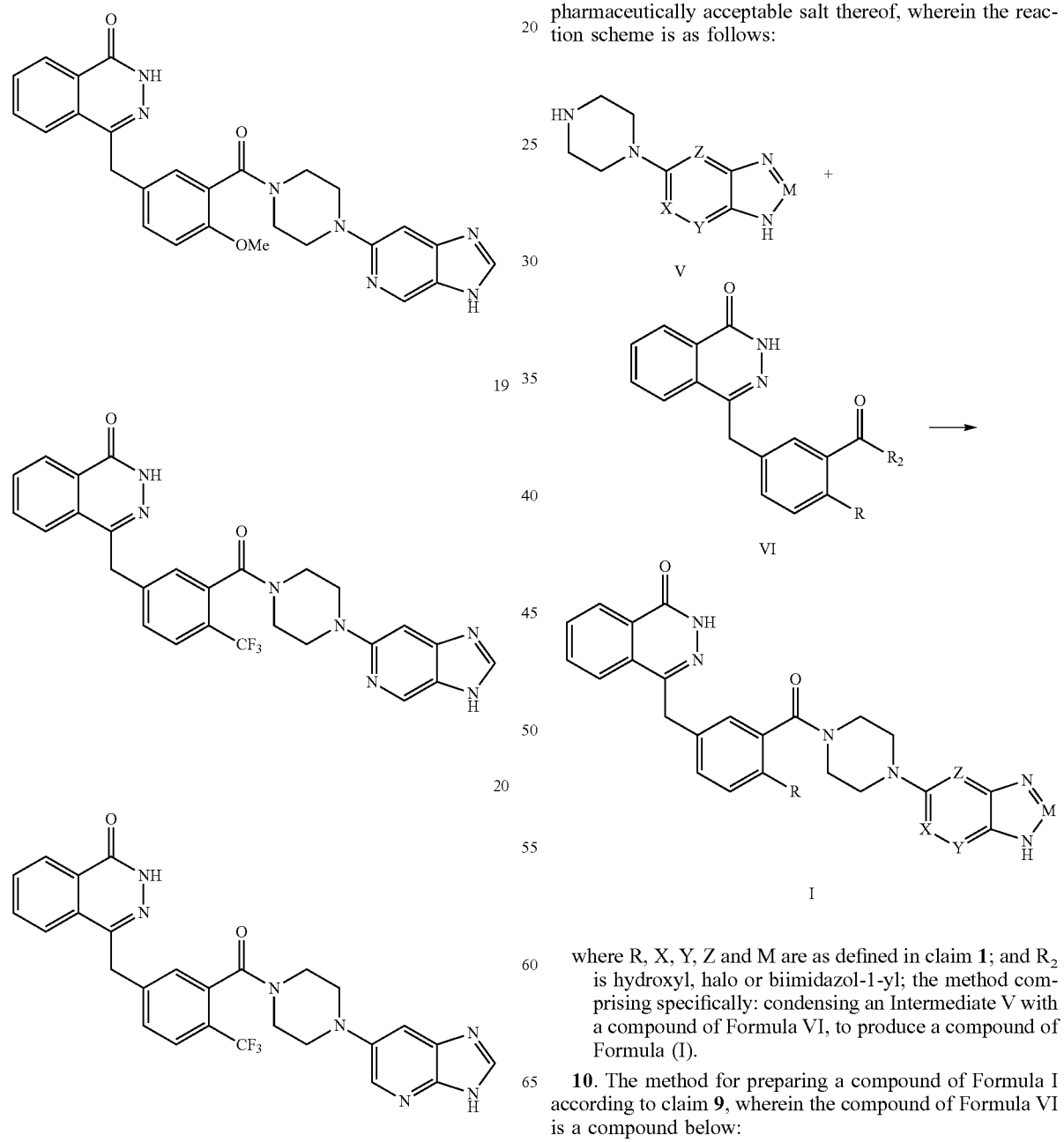

9. A method for preparing a compound of claim 1, or a pharmaceutically acceptable salt thereof, wherein the reaction scheme is as follows:

where R, X, Y, Z and M are as defined in claim 1; and $R_2$ is hydroxyl, halo or biimidazol-1-yl; the method comprising specifically: condensing an Intermediate V with a compound of Formula VI, to produce a compound of Formula (I).

10. The method for preparing a compound of Formula I according to claim 9, wherein the compound of Formula VI is a compound below:

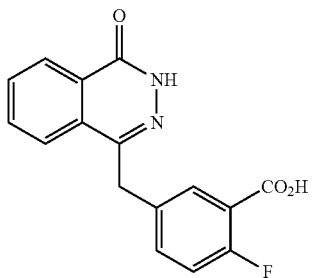

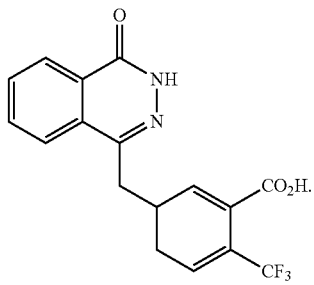

11. The method for preparing a compound of claim 9, wherein the condensing agent used in the condensation reaction is selected from the group consisting of 1,1'-carbonyl diimidazole, 1-ethyl-(3-dimethylaminopropyl) carbodiimide hydrochloride, 2-(7-azabenzotriazolyl)-N,N,N',N'-tetramethyluronium hexafluorophosphate, and benzotriazole-N,N,N',N'-tetramethyluronium hexafluorophosphate.

12. A method of treating a cancer in a subject, comprising administering a compound of claim 1 or a pharmaceutically acceptable salt thereof to a subject in need of treatment thereof, wherein the cancer is breast cancer or ovarian cancer.

13. The method of claim 12, wherein the cancer is deficient in Homologous Recombination (HR) dependent DNA double strand break (DSB) repair.

14. The method of claim 12, wherein the cancer comprises one or more cancer cells having a reduced or abrogated ability to repair DNA DSB by HR relative to normal cells.

15. The method of claim 12, wherein the cancer is one having a BRCA-1 or BRCA-2 deficient mutant phenotype.

16. The method of claim 12, wherein the cancer is a BRCA1 or/and BRCA2 deficient mutant cancer.

* * * * *